US011597779B2

(12) United States Patent
Jinzarli et al.

(10) Patent No.: US 11,597,779 B2
(45) Date of Patent: Mar. 7, 2023

(54) METHODS FOR PRODUCING A VISCOSE DOPE FROM MICROBIAL CELLULOSE

(71) Applicant: Nanollose Limited, Nedlands (AU)

(72) Inventors: Madian Mohamad Jinzarli, Nedlands (AU); Gary Andrew Cass, Nollamara (AU); John Moursounidis, Murdoch (AU); Wayne Morris Best, Gosnells (AU)

(73) Assignee: Nanollose Limited, Nedlands (AU)

(*) Notice: Subject to any disclaimer, the term of this patent is extended or adjusted under 35 U.S.C. 154(b) by 238 days.

(21) Appl. No.: 16/769,721

(22) PCT Filed: Nov. 30, 2018

(86) PCT No.: PCT/AU2018/051281
§ 371 (c)(1),
(2) Date: Jun. 4, 2020

(87) PCT Pub. No.: WO2019/109133
PCT Pub. Date: Jun. 13, 2019

(65) Prior Publication Data
US 2020/0369786 A1    Nov. 26, 2020

(30) Foreign Application Priority Data

Dec. 4, 2017 (AU) ............................... 2017904876
May 22, 2018 (AU) ............................... 2018901789

(51) Int. Cl.
| C08B 1/00 | (2006.01) |
| D01F 2/08 | (2006.01) |
| D21H 11/18 | (2006.01) |
| D21H 11/20 | (2006.01) |

(52) U.S. Cl.
CPC ............... *C08B 1/003* (2013.01); *D01F 2/08* (2013.01); *D21H 11/18* (2013.01); *D21H 11/20* (2013.01)

(58) Field of Classification Search
CPC ................................................. C08B 1/003
IPC ................................. D21C 3/22; D21H 11/20
See application file for complete search history.

(56) References Cited

U.S. PATENT DOCUMENTS

| 1,548,864 | A | | 8/1925 | Brandenberger |
| 4,123,381 | A | * | 10/1978 | Morishita .......... B01J 20/28026 |
| | | | | 427/213.36 |
| 4,605,517 | A | | 8/1986 | Riley et al. |
| 5,482,776 | A | * | 1/1996 | Nishiyama .............. D01F 2/06 |
| | | | | 428/397 |
| 8,383,529 | B2 | | 2/2013 | Ono et al. |
| 2012/0125547 | A1 | | 5/2012 | Akai |
| 2014/0186576 | A1 | | 7/2014 | Harmer et al. |

FOREIGN PATENT DOCUMENTS

| EP | 2395027 A1 | 12/2011 | |
| JP | 2017-095831 A | 6/2017 | |
| WO | WO-2001/086043 A1 | 11/2001 | |
| WO | WO-2006/004012 A1 | 1/2006 | |
| WO | WO-2006004012 A1 * | 1/2006 | ............. B01D 39/18 |
| WO | WO-2018/013034 A1 | 1/2018 | |
| WO | WO-2018/187841 A1 | 10/2018 | |

OTHER PUBLICATIONS

International Application No. PCT/AU2018/051281, International Search Report and Written Opinion, dated Feb. 7, 2019.
Czaja et al., Microbial cellulose—the natural power to heal wounds, Biomaterials, 27(2):145-51 (Jan. 2006).
Czaja, The future prospects of microbial cellulose in biomedical applications, Biomacromolecules, 8(1):1-12 (Jan. 2007).
Hestrin et al., Synthesis of cellulose by Acetobacter xylinum. II. Preparation of freeze-dried cells capable of polymerizing glucose to cellulose, Biochem J., 58(2):345-52 (Oct. 1954).
Hyden, Manufacture and properties of regenerated cellulose films, Ind. Eng. Chem., 21(5):405-10 (1929).
Mendes et al., In vivo and in vitro evaluation of an Acetobacter xylinum synthesized microbial cellulose membrane intended for guided tissue repair, Acta Veterinaria Scandinavica, 51:12 (2009).
Mihranyan, Cellulose from cladophorales green algae: From environmental problem to high-tech composite materials, J. Appl. Polymer Sci., 119(4):2449-60 (2011).

* cited by examiner

*Primary Examiner* — Leigh C Maier
*Assistant Examiner* — Everett White
(74) *Attorney, Agent, or Firm* — Marshall, Gerstein & Borun LLP

(57) ABSTRACT

A method for producing a microbial cellulose pulp for the production of viscose dope, the method comprising the step of: exposing a microbial cellulose to a volume of water to form the microbial cellulose pulp for the production of viscose dope, wherein the cellulose concentration in the microbial cellulose pulp is less than 0.040 g of cellulose per mL of pulp.

8 Claims, No Drawings

METHODS FOR PRODUCING A VISCOSE DOPE FROM MICROBIAL CELLULOSE

CROSS-REFERENCE TO RELATED APPLICATIONS

This application is a U.S. national phase of International Patent Application No. PCT/AU2018/051281, filed on 30 Nov. 2018, which claims priority benefit of Australian Patent Application No. 2018901789, filed on 22 May 2018, and Australian Patent Application No. 2017904876 filed on 4 Dec. 2017.

TECHNICAL FIELD

The present invention relates to a microbial cellulose pulp, a method for producing a microbial cellulose pulp, a method for mercerising a microbial cellulose pulp, a viscose dope produced from said microbial cellulose pulp using said method for mercerising a microbial cellulose pulp, a method for producing a viscose dope from said microbial cellulose pulp, and articles manufactured from said viscose dope, such as viscose rayon fibres and viscose sheeting.

BACKGROUND ART

Viscose rayon is a fibre consisting of regenerated cellulose, typically manufactured from plant cellulose using wood based cellulose pulp or cotton linters as the feed stock. Cellulose from these sources is extracted and purified to produce a pulp.

For existing feed stocks for the production of viscose fibre, the manufacture of viscose-grade cellulose pulp from wood is a time- and energy consuming process. For example, generating a cellulose pulp from wood necessitates barking and chipping trees before treating the wood in sodium hydroxide/sodium sulphide at elevated temperatures (for example, the Kraft process). Intensive forestry and the associated infrastructure is resource intensive, and continues to be challenged in meeting the growing demand for cellulose feedstock in industry.

To produce viscose dope, the cellulose pulp is first steeped in sodium hydroxide (typically 16-19%) in a process known as mercerising, to produce alkali cellulose (approximate formula $[C_6H_9O_4\text{—}ONa]_n$). Mercerising swells the pulp, which is essential for effective xanthation (described below).

Excess sodium hydroxide is then removed from the alkali cellulose (typically by pressing under vacuum), before the alkali cellulose is shredded and aged at controlled temperature and humidity. The aging process involves the reaction of oxygen with the cellulose polymers causing depolymerisation and thus affects the length of the cellulose polymers.

After aging, the solid alkali cellulose is reacted with carbon disulfide to form sodium cellulose xanthate, according to the equation:

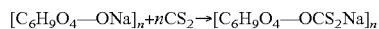

The xanthate groups of the cellulose xanthate render the cellulose xanthate more soluble: the more carbon disulfide that reacts with the alkali cellulose, the greater the solubility of the resulting sodium cellulose xanthate. The extent of substitution is often described by reference to a "gamma number". The gamma number refers to the number of xanthate groups per 100 anhydroglucose units (AGUs). As there are three hydroxyl groups on each anhydroglucose unit of cellulose, the maximum gamma number is 300.

The sodium cellulose xanthate is then dissolved in sodium hydroxide to produce a viscous cellulose xanthate solution known as a "viscose dope". The viscose dope may be aged or "ripened", during which the xanthate functionalisation distributes evenly on the cellulose chains, which is important for advantageous fibre properties. (See, for example, Wilkes, Andrew, 2001, "The Viscose Process", "In Regenerated Cellulose Fibres", edited by Calvin Woodings, p 37-61, Cambridge: Woodhead Publishing Ltd, the contents of which are incorporated by reference).

Viscose dope may be used to produce a number of products, including viscose rayon fibres (sometimes also known simply as viscose and/or rayon), and cellulose sheeting (sometimes known as cellophane).

Viscose rayon fibres are made by regenerating insoluble cellulose from the sodium cellulose xanthate by hydrolysing the xanthate groups responsible for the solubility of the cellulose with an acid, such as sulfuric acid.

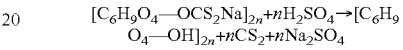

Fibres are produced by regenerating the insoluble cellulose as the viscose dope is forced through spinerettes into a bath of acid, typically with a coagulating agent such as $ZnSO_4$ and $Na_2SO_4$.

To enable the production of viscose rayon fibres from a viscose dope, the viscose dope must have certain properties. First, there is a practical lower limit to the concentration of cellulose in the viscose dope to enable the production of fibres. If the concentration of cellulose is too low, then the fibres, sheets, or other articles of manufacture will not be sufficiently durable. Typically, the concentration of cellulose in viscose dope used in industrially applied processes for the production of viscose rayon fibres is approximately 10%.

Secondly, at least in the case of production of viscose rayon fibres, the cellulose polymers in the viscose dope must be of a certain minimum length to provide fibres having adequate properties, such as tensile strength, elongation, absorbency, abrasion resistance, ease of dying. One parameter used to measure the size of cellulose xanthate polymers in viscose dope is the 'weight average molecular weight' $M_w$. $M_w$ takes into account the molecular weight of a chain in determining the contribution to the molecular weight average, in that the larger the polymer chain, the greater the contribution to the $M_w$. In industrially applied processes for the production of viscose rayon fibres, the Mw of the cellulose polymers is typically between about 150,000 and 200,000 $gmol^{-1}$. As such, any source of cellulose used for the manufacture of a viscose dope for the production of viscose rayon fibres must have an Mw in excess of this range.

Thirdly, the viscosity of the viscose dope must be amenable to being forced through the spinerettes to produce the fibres. The viscosity of the dope is a product of both the concentration of cellulose in the dope, and the length of the cellulose polymers, with higher concentrations and longer polymers causing higher viscosity. As noted above, the length of the polymers can be reduced by aging after mercerisation, but not increased.

Fourthly, the viscose dope must be free of particulate material, and or gel, or able to be filtered, to avoid blockage of the spinerettes.

The properties of a viscose dope are a function of both the various conditions under which the viscose dope is produced, such as the aging of the alkali cellulose and the ripening of the viscose dope, and the characteristics of the cellulose starting material. The methods of the present invention enable the production of a viscose dope from a microbial cellulose, wherein the viscose dope is suitable for the production of viscose rayon fibres, viscose sheets, and other articles of manufacture for which viscose dope having properties appropriate for viscose rayon and viscose sheet manufacture is suitable.

The present invention seeks to overcome, or at least ameliorate, one or more of the deficiencies of the prior art mentioned above, or to provide a useful or commercial choice.

The preceding discussion of the background art is intended to facilitate an understanding of the present invention only. The discussion is not an acknowledgement or admission that any of the material referred to is or was part of the common general knowledge as at the priority date of the application.

SUMMARY OF INVENTION

While there are a number of potential sources of cellulose, the most commonly used are wood pulp and cotton linters. Microbial cellulose provides a sustainable alternative to traditional cellulose sources, such as wood pulp or cotton linters, for the production of cellulose pulp for the production of viscose dope.

Cellulose from wood pulp and cotton linters are well characterised starting materials, and the key process parameters for producing viscose dope suitable from such are well known, and widely accepted, with viscose production facilities optimising their processes for the production of cellulose pulp and viscose dope produced by one of these two sources.

However, as will be explained in more detail in the following description of the invention, microbial cellulose has been discovered by the inventors to have different properties to cellulose derived from these traditional sources, with some of those different properties rendering ineffective the conventional approaches to the production of viscose dope.

Further, the inventors have discovered that in some cases it is simply not possible to achieve the process parameters considered necessary for the production of viscose dope from traditional sources using microbial cellulose as a cellulose source. Nonetheless, the inventors have discovered that viscose dope may be produced from microbial cellulose without achieving the process parameters previously considered necessary.

Further, the inventors have discovered that cellulose pulp suitable for the production of viscose dope can be produced from microbial cellulose using techniques that are considerably less energy-, water-, chemical- and/or waste management-intensive than conventional techniques for the production of cellulose pulp from wood, such as the Kraft process.

Thus, the inventors have discovered methods for the production of cellulose pulp from microbial cellulose, said microbial cellulose pulp being capable of producing viscose dope. The inventors have further discovered methods for the production of viscose dope from said microbial cellulose pulp. In highly preferred forms of the present invention, the viscose dope produced by the methods of the present invention is suitable for the production of viscose rayon fibres. In further highly preferred forms of the present invention, the viscose dope produced by the methods of the present invention is suitable for the production of viscose sheets.

Microbial cellulose pulps of the invention contain cellulose polymers having higher molecular weights, and more uniform molecular weight distributions, than those produced from conventional sources.

In a first aspect of the invention, there is provided a microbial cellulose pulp, wherein, the weight average molecular weight (Mw) is greater than 700 000 g mol$^{-1}$.

In a second aspect of the present invention there is provided a microbial cellulose pulp, wherein the polydispersity index is less than 4.5.

As would be understood by a person skilled in the art, the polydispersity index is a measure of the breadth of the molecular weight distribution of a polymer, and is defined as the weight average molecular weight, divided by the number average molecular weight (PD=Mw/Mn). A larger polydispersity index corresponds to a broader molecular weight range, and a polydispersity index of 1 corresponds to all polymers having equal chain lengths.

Preferably, the cellulose concentration in the microbial cellulose pulp is less than 0.040 g of cellulose per mL of pulp. More preferably, the cellulose concentration in the microbial cellulose pulp is less than 0.030 g of cellulose per mL of pulp. Still preferably, the cellulose concentration in the microbial cellulose pulp is less than 0.020 g of cellulose per mL of pulp.

Preferably, the microbial cellulose pulp is suitable for the production of a viscose dope.

As would be appreciated by a person skilled in the art, microbial cellulose exhibits a number of physical properties that significantly differ from cellulose derived from wood pulp, including high hydrophilicity, high degree of polymerisation (DP) and strong wet-web strength. In particular, the inventors consider that the high hydrophilicity of microbial cellulose is due to the higher surface area of what the inventors have discovered to be thinner fibrils giving rise to higher porosity, hence requiring more water to produce a fluid pulp. The greater degree of polymerisation means more reactive hydroxyl groups and a higher hydrophilicity. Further, the inventors have discovered that microbial cellulose has a higher crystallinity index which means less amorphous regions and greater efficiency at absorbing water.

The surprisingly different properties of microbial cellulose relative to cellulose derived from wood have been found by the inventors to significantly affect the ability to produce viscose dope from the microbial cellulose. For example, the water absorption capacity of microbial cellulose has been found to limit the cellulose concentration in the microbial cellulose pulp of the present invention. In particular, it has been found that pulps with a cellulose concentration greater than 0.040 g of cellulose per mL of pulp exhibit handling properties that are highly undesirable for further processing. Importantly, the inventors have found that mercerising pulps derived from microbial cellulose with a concentration greater than 4.0% w/w (40 gL$^{-1}$.) results in aggregation of the cellulose, which prevents adequate reaction of the cellulose with the sodium hydroxide during mercerisation. By way of comparison, even a 7.0% w/w solution of cellulose derived from wood remains a free-flowing fluid pulp.

The inventors have found that the pulping of microbial cellulose with water prior to the contact with sodium hydroxide during mercerisation is essential to its suitability for the production of a viscose dope. As discussed above, microbial cellulose forms as a dense matrix of thinner fibrils. It has been found by the inventors that if the microbial cellulose has not been pulped prior to the mercerisation step, then the mercerisation reaction only occurs at the surface of the dense matrix, leading to "gelling" of the outer surface and preventing any further reaction within the cellulose solid matrix. As would be appreciated by a person skilled in the art, this is different to typical methods for producing a viscose dope from cellulose derived from wood where the cellulose is not pulped prior to the mercerisation step. When contacted with sodium hydroxide, cellulose derived from wood does not exhibit this gelling. Without wishing to be bound by theory, the inventors understand that the cellulose macrostructure is porous enough to absorb sufficient sodium hydroxide solution to complete the mercerisation reaction.

In a third aspect of the present invention, there is provided a method for producing a microbial cellulose pulp for the production of viscose dope, the method comprising the step of:

exposing a microbial cellulose to a volume of water to form the microbial cellulose pulp for the production of viscose dope, wherein the cellulose concentration in the microbial cellulose pulp is less than 0.040 g of cellulose per mL of pulp.

Preferably, the cellulose concentration in the microbial cellulose pulp is less than 0.030 g of cellulose per mL of pulp. More preferably, the cellulose concentration in the microbial cellulose pulp is less than 0.020 g of cellulose per mL of pulp.

Preferably, the microbial cellulose pulp of the third aspect of the invention has the properties of the microbial cellulose pulp of the first and second aspects of the invention.

In a fourth aspect of the invention, there is provided a method for mercerising a microbial cellulose pulp, the method comprising the step of:

Exposing the microbial cellulose pulp to a quantity of sodium hydroxide solution, wherein the cellulose concentration in the mixture of microbial cellulose pulp and sodium hydroxide solution is less than 0.035 g of cellulose per mL of mixture.

Throughout this specification, unless the context requires otherwise, the terms "mercerising", "mercerisation" or variations thereof, will be understood to refer to a process that comprises the exposure of a cellulose containing material, particularly a microbial cellulose pulp, to sodium hydroxide. As would be appreciated by a person skilled in the art, the exposure of a cellulose containing material to sodium hydroxide allows for effective xanthation during the production of a viscose dope.

In a fifth aspect of the present invention, there is provided a method for producing a viscose dope, the method comprising the step of mercerising a microbial cellulose pulp in accordance with the abovementioned method.

Preferably the viscose dope is suitable for the production of viscose rayon fibres.

Preferably the viscose dope is suitable for the production of a viscose sheet.

In a sixth aspect of the present invention, there is provided a microbial cellulose pulp, produced by the method for producing a microbial cellulose pulp of the third aspect of the present invention.

In a seventh aspect of the invention, there is provided a mixture of microbial cellulose pulp and sodium hydroxide solution produced by the fifth aspect of the invention.

In an eighth aspect of the present invention, there is provided a method for the production of a viscose dope using a microbial cellulose pulp of the third aspect of the invention.

In a ninth aspect of the invention, there is provided a method for the production of viscose dope using a mixture of microbial cellulose pulp and sodium hydroxide solution produced by the fourth aspect of the invention.

In an tenth aspect of the present invention, there is provided a viscose dope, produced by the method for the production of a viscose dope of the fifth or ninth aspects of the present invention.

In an eleventh aspect of the present invention, there is provided a method for producing an article of manufacture from the viscose dope of the tenth aspect of the present invention.

In one form of the invention, the article of manufacture is a viscose rayon fibre. In one form of the invention, the article of manufacture is a viscose sheet.

In a twelfth aspect of the invention, there is provided an article of manufacture produced by the method of the eleventh aspect of the invention.

DETAILED DESCRIPTION OF EMBODIMENTS OF THE INVENTION

As described above, in one aspect of the invention, there is provided a method for the production of a viscose dope using a microbial cellulose pulp, the method comprising the step of producing the microbial cellulose pulp by: exposing a microbial cellulose to a volume of water to form the microbial cellulose pulp for the production of viscose dope, wherein the cellulose concentration in the microbial cellulose pulp is less than 0.040 g of cellulose per mL of pulp.

More preferably, the cellulose concentration in the microbial cellulose pulp is less than 0.030 g of cellulose per mL of pulp. Still preferably, the cellulose concentration in the microbial cellulose pulp is less than 0.020 g of cellulose per mL of pulp.

Microbial Cellulose Pulp

In a preferred form of the invention, the weight average molecular weight (Mw) of the cellulose in the microbial cellulose pulp is greater than 700 000 g mol$^{-1}$. Preferably, the weight average molecular weight (Mw) is greater than 800 000 g mol$^{-1}$. Preferably, the weight average molecular weight (Mw) is greater than 900 000 g mol$^{-1}$. Preferably, the weight average molecular weight (Mw) is greater than 1 000 000 g mol$^{-1}$. In particular embodiments of the invention, the Mw is less than 2 000 000 g mol$^{-1}$. In particular embodiments of the invention, the Mw is less than 1 500 000 g mol$^{-1}$.

The weight average molecular weight may be measured by gel permeation chromatography, a technique described in, for example "An Introduction to Gel Permeation Chromatography and Size Exclusion Chromatography", Agilent Technologies, 2015, https://www.agilent.com/cs/library/primers/Public/5990-6969EN%20GPC%20SEC%20Chrom%20Guide.pdf; and More S, Barth H G, "Size Exclusion Chromatography", 1st ed. Berlin (Ger), Springer-Verlag Berlin and Heidelberg GmbH & Co. KG. 199, p 234, the contents of which are incorporated by reference.

Gel permeation chromatography is also known as size exclusion chromatography (SEC) and gel filtration chromatography (GFC).

Alternate techniques for the determination of Mw include measuring the intrinsic viscosity and then applying the Mark-Houwink Equation:

$$[\eta]=KM^a$$

where a and K depend on the polymer-solvent system, as described below.

The intrinsic viscosity is measured using an Ubbelohde (AKA Ostwald, or "U-tube") Viscometer or equivalent instrument. This technique is used in conjunction with size exclusion chromatography as the intrinsic viscosity of a polymer is directly related to the elution volume of the polymer. Therefore, by running several monodisperse samples of polymer in a size exclusion chromatograph the values of K and a can be determined graphically using a line of best fit. Then the molecular weight and intrinsic viscosity relationship is defined.

In one embodiment of the invention, the weight average molecular weight (Mw) of the cellulose in the microbial cellulose pulp, as described above, is determined by one or more of these techniques. In a preferred embodiment of the invention, the Mw is determined using gel permeation chromatography.

In one aspect of the present invention the polydispersity index of the cellulose in the microbial cellulose pulp is less than about 4.5. Preferably, the polydispersity index is less than about 4.0.

In one form of the invention, the polydispersity index is less than 4.5. Preferably, the polydispersity index is less than 4.

In one form of the invention, the polydispersity index is between about 2 and about 4. In one form of the invention, the polydispersity index is between about 3 and about 4.

In one form of the invention, the polydispersity index is between 2 and 4. In one form of the invention, the polydispersity index is between 3 and 4.

The polydispersity of the cellulose in a cellulose pulp can be calculated from measurements generated using the same techniques for the measurement of the Mw of the cellulose. In one embodiment of the invention, the polydispersity of the cellulose, as described above, is determined by one or more of these techniques. In a preferred embodiment of the invention, the Mw is determined using gel permeation chromatography.

Preferably, the microbial cellulose pulp is suitable for the production of a viscose dope.

Preferably, the microbial cellulose pulp is suitable for the production of a viscose dope suitable for the production of viscose rayon fibres.

Preferably, the microbial cellulose pulp is suitable for the production of a viscose dope suitable for the production of cellulose sheeting.

In preferred forms of the invention, after the step of exposing a microbial cellulose to a volume of water to form the microbial cellulose pulp, the method for producing a microbial cellulose pulp comprises the step of:
homogenising the microbial cellulose pulp.

Throughout this specification, unless the context requires otherwise, the term "homogenisation process" or variations thereof, will be understood to refer to a process that decreases the particle size of least one fraction of a mixture containing at least two discrete fractions. In the context of the present invention, the homogenisation process reduces the average particle size of the microbial cellulose. The homogenising process does not necessarily result in a fully homogenous mixture.

Preferably, the step of homogenising the microbial cellulose pulp utilises a homogenisation process selected from any one of mechanical, ultrasound or pressure homogenisation processes, or a combination thereof. More preferably, the homogenisation process is a mechanical homogenisation process.

In one form of the present invention, where the homogenisation process more specifically comprises a mechanical homogenisation process, the microbial cellulose is deformed and/or broken under a stress applied by a mechanical force. The mechanical force may be selected from one or more of a tensile stress, bending stress, compressive stress, torsional stress, impact stress and shearing stress. Preferably, the mechanical force is any one of compressive stress, impact stress and shearing stress.

The inventors have found that mechanical homogenisation using high speed rotating blades is particularly useful in homogenisation of the microbial cellulose. In such processing, it is understood that the mechanical force primarily consists of the impact force generated from the collision between the rotating blades and the microbial cellulose and of the shearing force generated due to differences of the speed in the medium. Other forms of mechanical homogenisation apparatus include friction grinders. In such apparatus, the material is ground between two parallel grinding discs.

It has been found that subjecting the wet microbial cellulose to a homogenising process reduces the particle size of the microbial cellulose. This reduced particle size has been found to improve the suitability of the microbial cellulose pulp for mercerisation, such as occurs when microbial cellulose pulp is used for the production of viscose dope. The inventors have found that when subjecting a microbial cellulose pulp to a mercerisation step, gelatinous aggregates can form in the mercerised pulp. Without wishing to be bound by theory, the inventors believe that if the microbial cellulose is not homogenised adequately, aggregations of cellulose fibrils can remain throughout the pulp. Due to the dense packing of such aggregation, it is only the outer layer that is exposed to NaOH during mercerisation. This results in gelatinous aggregates that comprise a poorly mercerised microbial cellulose core. These poorly mercerised gelatinous aggregates do not xanthate properly and subsequently do not dissolve. As such, the majority of such aggregates will typically need to be removed prior to xanthation. The inventors have found that the reduction in particle size of the microbial cellulose prior to the mercerisation step will reduce the formation of such gelatinous aggregates. As discussed above, the inventors have found that the microbial cellulose consists of a dense network of thinner fibrils. Without wishing to be bound by theory, the inventors believe that the reduction in particle size will fibrillate the dense microbial cellulose network, thereby allowing greater exposure of the cellulose to the sodium hydroxide solution.

Methods of determining the size of particles are well known in the art. For example, the general method of U.S. Pat. No. 4,605,517, incorporated herein by reference, could be employed. The following is a description of one non-limiting method.

The particle size of the cellulose in the microbial cellulose pulp may be characterised for size using an instrument adapted to measure equivalent spherical volume diameter, e.g., a Horiba LA910 Laser Scattering Particle Size Distribution Analyzer, a Malvern Mastersizer 2000, or an equivalent instrument.

As would be understood by a person skilled in the art, particle size distributions are often measured by laser diffraction analysis, and expressed using D values. The meanings of the respective D values, are:
D10: size under which 10% by weight of the particles are below;
D50: size under which 50% by weight of the particles are below; and
D90: size under which 90% by weight of the particles are below.

Throughout this specification, references to particle size distribution characteristics refer to characteristics measured by laser diffraction analysis.

In one form of the invention, the D90, D50 and D10 values reported herein are evaluated using a Horiba LA910 Laser Scattering Particle Size Distribution Analyzer, a Malvern Mastersizer 2000 or other such equipment recognized by those skilled in the art. Using such instrument values for a suspension of the particles of unknown size are obtained, and the instrument is monitored using a control sample having particles within the size range expected based on statistical analysis of the control sample.

In a specific form of the present invention, the particles size distribution is calculated using a Mastersizer 2000 (Malvern, UK) laser diffractometer. More preferably, the operation conditions of the Mastersizer 2000 (Malvern, UK) laser diffractometer are as follows:
Laser particle sizer: Malvern Mastersizer 2000
Unit: Hydro 2000SM liquid route
Volume of the dispersing carrier fluid: 150 ml
Wavelengths (blue and red): 466 and 632 nm
Stirring speed: 1950 rev/min
Analytical range: 0.02 µm to 2000 µm
Optical model (Mie theory)
Values of the refractive indices used:
Dispersing fluid (water) $n_{fluid}$=1.33+i0
Values of the obscuration Between 10% and 20%
Acquisition time 10 s In a preferred form of the invention, the D90 is less than 1700 µm. In a preferred form of the invention, the D90 is less than 1600 µm. In a preferred form of the invention, the particle size distribution of the particles of cellulose in the pulp is such that the D90 is less than 1500 µm. In a preferred form of the invention, the D90 is less than 1400 µm. In a preferred form of the invention, the D90 is less than 1300 µm. In a preferred form of the invention, the D90 is less than 1200 µm. In a preferred form of the invention, the D90 is less than 1100 µm. In a preferred form of the invention, the D90 is less than 1000 µm. In a preferred form of the invention, the D90 is less than 900 µm. In a preferred form of the invention, the D90 is less than 800 µm. In a preferred form of the invention, the D90 is less than 700 µm. In a preferred form of the invention, the D90 is less than 600 µm. In a preferred form of the invention, the D90 is less than 500 µm. In a preferred form of the invention, the D90 is less than 400 µm. In a preferred form of the invention, the D90 is less than 300 µm. In a preferred form of the invention, the D90 is less than 200 µm. In a preferred form of the invention, the D90 is less than 100 µm.

In a preferred form of the invention, the particle size distribution of the particles of cellulose in the pulp is such that the D90 is between 100 µm and 1700 µm. In a preferred form of the invention, the particle size distribution of the particles of cellulose in the pulp is such that the D90 is between 100 µm and 1600 µm. In a preferred form of the invention, the particle size distribution of the particles of cellulose in the pulp is such that the D90 is between 100 µm and 1500 µm. In a preferred form of the invention, the D90 is between 100 µm and 1400 µm. In a preferred form of the invention, the D90 is between 100 µm and 1300 µm. In a preferred form of the invention, the D90 is between 100 µm and 1200 µm. In a preferred form of the invention, the D90 is between 100 µm and 1500 µm. In a preferred form of the invention, the D90 is between 100 µm and 1000 µm. In a preferred form of the invention, the D90 is between 100 µm and 900 µm. In a preferred form of the invention, the D90 is between 100 µm and 800 µm. In a preferred form of the invention, the D90 is between 100 µm and 700 µm. In a preferred form of the invention, the D90 is between 100 µm and 600 µm. In a preferred form of the invention, the D90 is between 100 µm and 500 µm.

In a preferred form of the invention, the D50 is less than 1200 µm. In a preferred form of the invention, the D50 is less than 1100 µm. In a preferred form of the invention, the D50 is less than 1000 µm. In a preferred form of the invention, the D50 is less than 900 µm. In a preferred form of the invention, the D50 is less than 800 µm. In a preferred form of the invention, the D50 is less than 700 µm. In a preferred form of the invention, the D50 is less than 600 µm. In a preferred form of the invention, the D50 is less than 500 µm. In a preferred form of the invention, the D50 is less than 400 µm. In a preferred form of the invention, the D50 is less than 300 µm. In a preferred form of the invention, the D50 is less than 200 µm. In a preferred form of the invention, the D50 is less than 100 µm. In a preferred form of the invention, the D50 is less than 90 µm. In a preferred form of the invention, the D50 is less than 80 µm. In a preferred form of the invention, the D50 is less than 70 µm. In a preferred form of the invention, the D50 is less than 60 µm. In a preferred form of the invention, the D50 is less than 50 µm In a preferred form of the invention, the D50 is less than 40 µm.

In a preferred form of the invention, the particle size distribution of the particles of microbial cellulose in the pulp is such that the D50 is between 40 and 1100 µm. In a preferred form of the invention, the D50 is between 40 and 1000 µm. In a preferred form of the invention, the D50 is between 40 and 900 µm. In a preferred form of the invention, the D50 is between 40 and 800 µm. In a preferred form of the invention, the D50 is between 40 and 700 µm. In a preferred form of the invention, the D50 is between 40 and 600 µm. In a preferred form of the invention, the D50 is between 40 and 500 µm.

In a preferred form of the invention, the D10 is less than 500 µm. In a preferred form of the invention, the D10 is less than 400 µm. In a preferred form of the invention, the D10 is less than 300 µm. In a preferred form of the invention, the D10 is less than 200 µm. In a preferred form of the invention, the D10 is less than 100 µm. In a preferred form of the invention, the D10 is less than 90 µm. In a preferred form of the invention, the D10 is less than 80 µm. In a preferred form of the invention, the D10 is less than 70 µm. In a preferred form of the invention, the D10 is less than 60 µm. In a preferred form of the invention, the D10 is less than 50 µm. In a preferred form of the invention, the D10 is less than 40 µm. In a preferred form of the invention, the D10 is less than 30 µm. In a preferred form of the invention, the D10 is less than 20 µm. In a preferred form of the invention, the D10 is less than 10 µm. In a preferred form of the invention, the D10 is less than 5 µm. In a preferred form of the invention, the D10 is less than 2 µm. In a preferred form of the invention, the D10 is less than 1 µm. In a preferred form of the invention, the D10 is less than 0.5 µm.

In a preferred form of the invention, the particle size distribution of the particles of microbial cellulose in the pulp is such that the D10 is between 1 and 150 µm. In a preferred form of the invention, the D10 is between 1 and 140 µm. In a preferred form of the invention, the D10 is between 1 and 130 µm. In a preferred form of the invention, the D10 is between 1 and 120 µm. In a preferred form of the invention, the D10 is between 1 and 110 µm. In a preferred form of the invention, the D10 is between 1 and 100 µm. In a preferred form of the invention, the D10 is between 1 and 90 µm. In a preferred form of the invention, the D10 is between 1 and 80 µm.

In one form of the present invention, the D10 is below 800 µm, the D50 is below 1200 µm and the D90 is below 1700 µm. In a preferred form of the present invention, the D10 is below 600 µm, the D50 is below 800 µm and the D90 is below 1400 µm. In a preferred form of the present invention, the D10 is below 100 µm, the D50 is below 500 µm and the D90 is below 1200 µm. In a preferred form of the present invention, the D10 is below 50 µm, the D50 is below 300 µm and the D90 is below 1000 µm.

Mercerising a Microbial Cellulose Pulp

In one aspect of the invention, the method for the production of a viscose dope using a microbial cellulose pulp comprises the step of mercerising the microbial cellulose pulp by exposing the microbial cellulose pulp to sodium hydroxide.

The sodium hydroxide may be in solid form, or in a solution. In preferred forms of the invention, the sodium hydroxide is in an aqueous solution.

In one form of the invention, the step of mercerising the microbial cellulose pulp comprises the step of:

exposing the microbial cellulose pulp to a sodium hydroxide solution, wherein the cellulose concentration in the mixture of microbial cellulose pulp and sodium hydroxide solution is less than about 0.35 g of cellulose per mL of mixture.

In one form of the invention, the step of mercerising the microbial cellulose pulp comprises:

exposing the microbial cellulose pulp to a quantity of sodium hydroxide solution, wherein the cellulose concentration in the mixture of microbial cellulose pulp and sodium hydroxide solution is less than 0.35 g of cellulose per mL of mixture.

As would be appreciated by a person skilled in the art, when using cellulose derived from wood pulp, the cellulose concentration in the mercerisation solution is selected to ensure that there is sufficient sodium hydroxide solution for a given mass of cellulose, without having a significant excess of free sodium hydroxide. Typical cellulose concentrations are in the range of 2.5%-7%, depending on the equipment used. As discussed above, microbial cellulose exhibits significantly different physical properties to cellulose derived from wood. These physical properties have been found to limit the cellulose concentration in the mixture of microbial cellulose pulp and sodium hydroxide solution. By limiting the concentration of microbial cellulose, the inventors have found that the microbial cellulose pulp remains free flowing, thereby ensuring adequate mixing of the microbial cellulose and the sodium hydroxide solution. In one form of the invention, prior to the step of exposing the microbial cellulose pulp to a quantity of sodium hydroxide solution, wherein the cellulose concentration in the mixture of microbial cellulose pulp and sodium hydroxide solution is less than 0.35 g of cellulose per mL of mixture, the method may comprise the step of:

concentrating the microbial cellulose pulp by removing water therefrom.

The step of concentrating the microbial cellulose pulp by removing water therefrom may be performed by means of evaporation of water, including evaporation under reduced pressure and or heating, or by physical separation such as filtration or spinning, or combinations thereof.

In a preferred form of the invention, the step of concentrating the microbial cellulose pulp by removing water therefrom is performed by spinning the microbial cellulose pulp.

In a preferred form of the invention, the cellulose concentration in the mixture of microbial cellulose pulp and sodium hydroxide solution is less than about 0.295 g of cellulose per mL of mixture. In a preferred form of the invention, the cellulose concentration in the mixture of microbial cellulose pulp and sodium hydroxide solution is less than about 0.29 g of cellulose per mL of mixture. In a preferred form of the invention, the cellulose concentration in the mixture of microbial cellulose pulp and sodium hydroxide solution is less than about 0.285 g of cellulose per mL of mixture. In a preferred form of the invention, the cellulose concentration in the mixture of microbial cellulose pulp and sodium hydroxide solution is less than about 0.28 g of cellulose per mL of mixture. In a preferred form of the invention, the cellulose concentration in the mixture of microbial cellulose pulp and sodium hydroxide solution is less than about 0.275 g of cellulose per mL of mixture. In a preferred form of the invention, the cellulose concentration in the mixture of microbial cellulose pulp and sodium hydroxide solution is less than about 0.27 g of cellulose per mL of mixture. In a preferred form of the invention, the cellulose concentration in the mixture of microbial cellulose pulp and sodium hydroxide solution is less than about 0.265 g of cellulose per mL of mixture. In a preferred form of the invention, the cellulose concentration in the mixture of microbial cellulose pulp and sodium hydroxide solution is less than about 0.26 g of cellulose per mL of mixture. In a preferred form of the invention, the cellulose concentration in the mixture of microbial cellulose pulp and sodium hydroxide solution is less than about 0.255 g of cellulose per mL of mixture. In a preferred form of the invention, the cellulose concentration in the mixture of microbial cellulose pulp and sodium hydroxide solution is less than about 0.25 g of cellulose per mL of mixture. In a preferred form of the invention, the cellulose concentration in the mixture of microbial cellulose pulp and sodium hydroxide solution is less than about 0.245 g of cellulose per mL of mixture. In a preferred form of the invention, the cellulose concentration in the mixture of microbial cellulose pulp and sodium hydroxide solution is less than about 0.24 g of cellulose per mL of mixture. In a preferred form of the invention, the cellulose concentration in the mixture of microbial cellulose pulp and sodium hydroxide solution is less than about 0.235 g of cellulose per mL of mixture. In a preferred form of the invention, the cellulose concentration in the mixture of microbial cellulose pulp and sodium hydroxide solution is less than about 0.23 g of cellulose per mL of mixture. In a preferred form of the invention, the cellulose concentration in the mixture of microbial cellulose pulp and sodium hydroxide solution is less than about 0.225 g of cellulose per mL of mixture. In a preferred form of the invention, the cellulose concentration in the mixture of microbial cellulose pulp and sodium hydroxide solution is less than about 0.22 g of cellulose per mL of mixture. In a preferred form of the invention, the cellulose concentration in the mixture of microbial cellulose pulp and sodium hydroxide solution is less than about 0.215 g of cellulose per mL of mixture. In a preferred form of the invention, the cellulose concentration in the mixture of microbial cellulose pulp and sodium hydroxide solution is less than about 0.215 g of cellulose per mL of mixture. In a preferred form of the invention, the cellulose concentration in the mixture of microbial cellulose pulp and sodium hydroxide solution is less than about 0.205 g of cellulose per mL of mixture. In a preferred form of the invention, the cellulose concentration in the mixture of microbial cellulose pulp and sodium hydroxide solution is less than about 0.20 g of cellulose per mL of mixture. In a preferred form of the invention, the cellulose concentration in the mixture of microbial cellulose pulp and sodium hydroxide solution is less than about 0.195 g of cellulose per mL of mixture. In a preferred form of the invention, the cellulose concentration in the mixture of microbial cellulose pulp and sodium hydroxide solution is less than about 0.19 g of cellulose per mL of mixture. In a preferred form of the invention, the cellulose concentration in the mixture of microbial cellulose pulp and sodium hydroxide solution is less than about 0.185 g of cellulose per mL of mixture. In a preferred form of the invention, the cellulose concentration in the mixture of microbial cellulose pulp and sodium hydroxide solution is less than about 0.18 g of cellulose per mL of mixture. In a preferred form of the invention, the cellulose concentration in the mixture of microbial cellulose pulp and sodium hydroxide solution is less than about 0.175 g of cellulose per mL of mixture. In a preferred form of the invention, the cellulose concentration in the mixture of microbial cellulose pulp and sodium hydroxide solution is less than about 0.17 g of cellulose per mL of mixture. In a preferred form of the invention, the cellulose concentration in the mixture of microbial cellulose pulp and sodium hydroxide solution is less than about 0.165 g of cellulose per mL of mixture. In a preferred form of the invention, the cellulose concentration in the mixture of microbial cellulose pulp and sodium hydroxide solution is less than about 0.16 g of cellulose per mL of mixture. In a preferred form of the invention, the cellulose concentration in the mixture of microbial cellulose pulp and sodium hydroxide solution is less than about 0.155 g of cellulose per mL of mixture. In a preferred form of the invention, the cellulose concentration in the mixture of microbial cellulose pulp and sodium hydroxide solution is less than about 0.15 g of cellulose per mL of mixture. In a preferred form of the invention, the cellulose concentration in the mixture of microbial cellulose pulp and sodium hydroxide solution is less than about 0.145 g of cellulose per mL of mixture. In a preferred form of the invention, the cellulose concentration in the mixture of microbial cellulose pulp and sodium hydroxide solution is less than about 0.14 g of cellulose per mL of mixture. In a preferred form of the invention, the cellulose concentration in the mixture of microbial cellulose pulp and sodium hydroxide solution is less than about 0.135 g of cellulose per mL of mixture. In a preferred form of the invention, the cellulose concentration in the mixture of microbial cellulose pulp and sodium hydroxide solution is less than about 0.13 g of cellulose per mL of mixture. In a preferred form of the invention, the cellulose concentration in the mixture of microbial cellulose pulp and sodium hydroxide solution is less than about 0.125 g of cellulose per mL of mixture. In a preferred form of the invention, the cellulose concentration in the mixture of microbial cellulose pulp and sodium hydroxide solution is less than about 0.12 g of cellulose per mL of mixture. In a preferred form of the invention, the cellulose concentration in the mixture of microbial cellulose pulp and sodium hydroxide solution is less than about 0.115 g of cellulose per mL of mixture. In a preferred form of the invention, the cellulose concentration in the mixture of microbial cellulose pulp and sodium hydroxide solution is less than about 0.11 g of cellulose per mL of mixture. In a preferred form of the invention, the cellulose concentration in the mixture of microbial cellulose pulp and sodium hydroxide solution is less than about 0.105 g of cellulose per mL of mixture. In a preferred form of the invention, the cellulose concentration in the mixture of microbial cellulose pulp and sodium hydroxide solution is less than about 0.10 g of cellulose per mL of mixture. In a preferred form of the invention, the cellulose concentration in the mixture of microbial cellulose pulp and sodium hydroxide solution is less than about 0.095 g of cellulose per mL of mixture. In a preferred form of the invention, the cellulose concentration in the mixture of microbial cellulose pulp and sodium hydroxide solution is less than about 0.09 g of cellulose per mL of mixture. In a preferred form of the invention, the cellulose concentration in the mixture of microbial cellulose pulp and sodium hydroxide solution is less than about 0.085 g of cellulose per mL of mixture. In a preferred form of the invention, the cellulose concentration in the mixture of microbial cellulose pulp and sodium hydroxide solution is less than about 0.08 g of cellulose per mL of mixture. In a preferred form of the invention, the cellulose concentration in the mixture of microbial cellulose pulp and sodium hydroxide solution is less than about 0.075 g of cellulose per mL of mixture. In a preferred form of the invention, the cellulose concentration in the mixture of microbial cellulose pulp and sodium hydroxide solution is less than about 0.07 g of cellulose per mL of mixture.

Surprisingly, given the cellulose concentrations used in the production of conventional sources of cellulose, the inventors have discovered that mixtures of microbial cellulose pulp and sodium hydroxide solution with greater than 0.035 g of cellulose per mL of mixture of microbial cellulose pulp and sodium hydroxide solution typically exhibit handling properties that are highly undesirable for further processing, in some cases to the extent that the pulp did not behave as a fluid pulp at all, which prevented adequate reaction of the cellulose with the sodium hydroxide during mercerisation. At concentrations higher than 0.035 g of cellulose per mL of mixture, it may be possible to produce a mercerised pulp suitable for xanthation by selectively removing gelatinous aggregates (by, for example, sieving), however this will adversely impact on the efficiency of the conversion of the cellulose and, as such, is highly undesirable. A further approach is to selectively homogenise gelatinous aggregates, however this is an inefficient approach and not readily transferable to a commercial process.

In a preferred form of the invention, the cellulose concentration in the mixture of microbial cellulose pulp and sodium hydroxide solution is less than about 0.034 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.03 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.025 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.020 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.019 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.018 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.017 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.016 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.015 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.014 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.013 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.012 g of cellulose per mL of mixture of microbial cellulose pulp and sodium hydroxide solution. In a preferred form of the invention, the cellulose concentration in the mixture of microbial cellulose pulp and sodium hydroxide solution is less than about 0.011 g of cellulose per mL of mixture of microbial cellulose pulp and sodium hydroxide solution.

In a preferred form of the invention, the cellulose concentration in the mixture of microbial cellulose pulp and sodium hydroxide solution is less than 0.034 g of cellulose per mL of mixture of microbial cellulose pulp and sodium hydroxide solution. In a preferred form of the invention, the cellulose concentration in the mixture of microbial cellulose pulp and sodium hydroxide solution is less than 0.030 g of cellulose per mL of mixture of microbial cellulose pulp and sodium hydroxide solution. In a preferred form of the invention, the cellulose concentration in the mixture of microbial cellulose pulp and sodium hydroxide solution is less than 0.025 g of cellulose per mL of mixture of microbial cellulose pulp and sodium hydroxide solution. In a preferred form of the invention, the cellulose concentration in the mixture of microbial cellulose pulp and sodium hydroxide solution is less than 0.020 g of cellulose per mL of mixture of microbial cellulose pulp and sodium hydroxide solution. In a preferred form of the invention, the cellulose concentration in the mixture of microbial cellulose pulp and sodium hydroxide solution is less than 0.019 g of cellulose per mL of mixture of microbial cellulose pulp and sodium hydroxide solution. In a preferred form of the invention, the cellulose concentration in the mixture of microbial cellulose pulp and sodium hydroxide solution is less than 0.018 g of cellulose per mL of mixture of microbial cellulose pulp and sodium hydroxide solution. In a preferred form of the invention, the cellulose concentration in the mixture of microbial cellulose pulp and sodium hydroxide solution is less than 0.017 g of cellulose per mL of mixture of microbial cellulose pulp and sodium hydroxide solution. In a preferred form of the invention, the cellulose concentration in the mixture of microbial cellulose pulp and sodium hydroxide solution is less than 0.016 g of cellulose per mL of mixture of microbial cellulose pulp and sodium hydroxide solution. In a preferred form of the invention, the cellulose concentration in the mixture of microbial cellulose pulp and sodium hydroxide solution is less than 0.015 g of cellulose per mL of mixture of microbial cellulose pulp and sodium hydroxide solution. In a preferred form of the invention, the cellulose concentration in the mixture of microbial cellulose pulp and sodium hydroxide solution is less than 0.014 g of cellulose per mL of the mixture of microbial cellulose pulp and sodium hydroxide solution. In a preferred form of the invention, the cellulose concentration in the mixture of microbial cellulose pulp and sodium hydroxide solution is less than 0.013 g of cellulose per mL of the mixture of microbial cellulose pulp and sodium hydroxide solution. In a preferred form of the invention, the cellulose concentration in the mixture of microbial cellulose pulp and sodium hydroxide solution is less than 0.012 g of cellulose per mL of the mixture of microbial cellulose pulp and sodium hydroxide solution. In a preferred form of the invention, the cellulose concentration in the mixture of microbial cellulose pulp and sodium hydroxide solution is less than 0.011 g of cellulose per mL of the mixture of microbial cellulose pulp and sodium hydroxide solution.

In a highly preferred form of the invention, the cellulose concentration in the mixture of microbial cellulose pulp and sodium hydroxide solution is about 0.010 g of cellulose per mL of the mixture of microbial cellulose pulp and sodium hydroxide solution.

As noted above, at concentrations beyond about 0.035 g of cellulose per mL, the inventors have discovered that the physical properties of the mercerising mixture exhibit the properties of a gel or a wet solid, significantly inhibiting effective mercerisation of the pulp, an essential step in the production of viscose dope from cellulose pulp.

However, highly advantageously, the inventors have identified that this is not the case at concentrations about 0.010 g of cellulose per mL. At concentrations above about 0.010 g of cellulose per mL of pulp, but less than about 0.035 g of cellulose per mL of pulp it is possible to produce a viable pulp but it will be necessary to remove aggregates of gel, such as by screening, or by targeted or localised homogenisation. Targeted or localised homogenisation in a commercial context is unlikely to be practical. Removal of gel aggregates will detract from the efficiency of the conversion of source to pulp. At concentrations in excess of about 0.035 g of cellulose per mL of pulp, the inventors have discovered that it is practically impossible to produce a viable cellulose dope for the purpose of producing a viscose dope using commercially viable methodologies.

In one form of the invention, cellulose concentration in the mixture of microbial cellulose pulp and sodium hydroxide is more than 0.001 g of cellulose per mL of mixture of microbial cellulose pulp and sodium hydroxide. While lower concentrations such as this do not attract the undesirable physical properties mentioned above, low concentrations are generally undesirable, as they involve handling larger volumes of liquids. The inventors consider that cellulose concentration in the mixture of microbial cellulose pulp and sodium hydroxide is less than 0.001 g of cellulose per mL of pulp are unlikely to be commercially practical.

In a preferred form of the invention, the cellulose concentration in the mixture of microbial cellulose pulp and sodium hydroxide is more than about 0.002 g of cellulose per mL of mixture of microbial cellulose pulp and sodium hydroxide. In a preferred form of the invention, the cellulose concentration in the mixture of microbial cellulose pulp and sodium hydroxide is more than about 0.003 g of cellulose per mL of mixture of microbial cellulose pulp and sodium hydroxide. In a preferred form of the invention, cellulose concentration in the mixture of microbial cellulose pulp and sodium hydroxide is more than about 0.004 g of cellulose per mL of mixture of microbial cellulose pulp and sodium hydroxide. In a preferred form of the invention, the cellulose concentration in the mixture of microbial cellulose pulp and sodium hydroxide is more than about 0.005 g of cellulose per mL of mixture of microbial cellulose pulp and sodium hydroxide. In a preferred form of the invention, cellulose concentration in the mixture of microbial cellulose pulp and sodium hydroxide is more than about 0.006 g of cellulose per mL of mixture of microbial cellulose pulp and sodium hydroxide.

In a preferred form of the invention, the cellulose concentration in the mixture of microbial cellulose pulp and sodium hydroxide is more than 0.002 g of cellulose per mL of mixture of microbial cellulose pulp and sodium hydroxide. In a preferred form of the invention, the cellulose concentration in the mixture of microbial cellulose pulp and sodium hydroxide is more than 0.003 g of cellulose per mL of mixture of microbial cellulose pulp and sodium hydroxide. In a preferred form of the invention, cellulose concentration in the mixture of microbial cellulose pulp and sodium hydroxide is more than 0.004 g of cellulose per mL of mixture of microbial cellulose pulp and sodium hydroxide. In a preferred form of the invention, the cellulose concentration in the mixture of microbial cellulose pulp and sodium hydroxide is more than 0.005 g of cellulose per mL of mixture of microbial cellulose pulp and sodium hydroxide. In a preferred form of the invention, cellulose concentration in the mixture of microbial cellulose pulp and sodium hydroxide is more than 0.006 g of cellulose per mL of mixture of microbial cellulose pulp and sodium hydroxide.

Techniques for mercerising cellulose pulps are known in the art. See, for example Wilkes A G. The Viscose Process. In: Woodings C, editor, "Regenerated Cellulose Fibres", 1st ed. Cambridge (UK), Woodhead Publishing Limited, 2001, p. 37-61, the contents of which are incorporated by reference.

In one form of the invention, the step of exposing the microbial cellulose pulp to a sodium hydroxide solution more specifically comprises exposing the microbial cellulose pulp to a sodium hydroxide solution such that the concentration of sodium hydroxide in the mixture of microbial cellulose pulp to a sodium hydroxide solution is between about 80 and about 500 g $L^{-1}$. In a more specific form of the invention, the concentration of sodium hydroxide in the mixture of microbial cellulose pulp to a sodium hydroxide solution is between about 90 and about 300 g $L^{-1}$. In a more specific form of the invention, the concentration of sodium hydroxide in the mixture of microbial cellulose pulp to a sodium hydroxide solution is between about 100 and about 200 g $L^{-1}$. In a more specific form of the invention, the concentration of sodium hydroxide in the mixture of microbial cellulose pulp to a sodium hydroxide solution is between about 100 and about 250 g $L^{-1}$. In a more specific form of the invention, the concentration of sodium hydroxide in the mixture of microbial cellulose pulp to a sodium hydroxide solution is between about 100 and about 200 g $L^{-1}$. In a more specific form of the invention, the concentration of sodium hydroxide in the mixture of microbial cellulose pulp to a sodium hydroxide solution is between about 170 and about 190 g $L^{-1}$. In a more specific form of the invention, the concentration of sodium hydroxide in the mixture of microbial cellulose pulp to a sodium hydroxide solution is about 180 g $L^{-1}$.

In one form of the invention, the step of exposing the microbial cellulose pulp to a sodium hydroxide solution more specifically comprises exposing the microbial cellulose pulp to a sodium hydroxide solution such that the concentration of sodium hydroxide in the mixture of microbial cellulose pulp to a sodium hydroxide solution is between 80 and 300 g $L^{-1}$. In a more specific form of the invention, the concentration of sodium hydroxide in the mixture of microbial cellulose pulp to a sodium hydroxide solution is between 90 and 300 g $L^{-1}$. In a more specific form of the invention, the concentration of sodium hydroxide in the mixture of microbial cellulose pulp to a sodium hydroxide solution is between 100 and 200 g $L^{-1}$. In a more specific form of the invention, the concentration of sodium hydroxide in the mixture of microbial cellulose pulp to a sodium hydroxide solution is between 100 and 250 g $L^{-1}$. In a more specific form of the invention, the concentration of sodium hydroxide in the mixture of microbial cellulose pulp to a sodium hydroxide solution is between 100 and 200 g $L^{-1}$. In a more specific form of the invention, the concentration of sodium hydroxide in the mixture of microbial cellulose pulp to a sodium hydroxide solution is between 170 and 190 g $L^{-1}$. In a more specific form of the invention, the concentration of sodium hydroxide in the mixture of microbial cellulose pulp to a sodium hydroxide solution is 180 g $L^{-1}$.

Preferred forms of the invention utilise more concentrated solutions of sodium hydroxide to reduce the overhead associated with handling larger volumes of solutions, and to reduce pressing demands. However, occupational health and safety considerations may impose an upper concentration limit.

Alternate forms of the invention may employ a technique known as "double-steeping", involving a second exposure to a less concentrated sodium hydroxide solution. After the first exposure, at the concentrations indicated above, the mixture is only lightly pressed prior to the second exposure, after which conventional pressing and shredding occurs.

In a preferred form of the invention, the step of exposing the microbial cellulose pulp to a sodium hydroxide solution more specifically comprises exposing the microbial cellulose pulp to a sodium hydroxide solution at a temperature between about 30 and about 70° C. Preferably still, the temperature is between 40 and 60° C. Preferably still, the temperature is between about 45 and about 55° C. In a specific form of the invention, the temperature is about 50° C.

In a preferred form of the invention, the step of exposing the microbial cellulose pulp to a sodium hydroxide solution more specifically comprises exposing the microbial cellulose pulp to a sodium hydroxide solution at a temperature between 30 and 70° C. Preferably still, the temperature is between 40 and 60° C. Preferably still, the temperature is between 45 and 55° C. In a specific form of the invention, the temperature is 50° C.

In a preferred form of the invention, the step of exposing the microbial cellulose pulp to a sodium hydroxide solution more specifically comprises exposing the microbial cellulose pulp to a sodium hydroxide solution at a temperature below 100° C. The inventors have discovered that at temperatures in excess of this, there is a propensity to generate solids, which is highly disadvantageous in the production of viscose dope.

In preferred forms of the present invention, the step of mercerizing the microbial cellulose pulp by exposing the microbial cellulose pulp to a sodium hydroxide solution takes place for a period of at least 60 minutes. Preferably still, the step of mercerizing the microbial cellulose pulp by exposing the microbial cellulose pulp to a sodium hydroxide solution takes place for a period of at least 90 minutes. Preferably still, the step of mercerizing the microbial cellulose pulp by exposing the microbial cellulose pulp to a sodium hydroxide solution takes place for a period of at least 120 minutes.

The inventors consider that the commercially practical upper limit for such a process is 24 hours. Preferably, the step of mercerizing the microbial cellulose pulp by exposing the microbial cellulose pulp to a sodium hydroxide solution takes place for a period of less than 24 hours. Preferably still, the step of mercerizing the microbial cellulose pulp by exposing the microbial cellulose pulp to a sodium hydroxide solution takes place for a period of less than 18 hours. Preferably still, the step of mercerizing the microbial cellulose pulp by exposing the microbial cellulose pulp to a sodium hydroxide solution takes place for a period of less than 15 hours. Preferably still, the step of mercerizing the microbial cellulose pulp by exposing the microbial cellulose pulp to a sodium hydroxide solution takes place for a period of less than 12 hours. Preferably still, the step of mercerizing the microbial cellulose pulp by exposing the microbial cellulose pulp to a sodium hydroxide solution takes place for a period of less than 9 hours. Preferably still, the step of mercerizing the microbial cellulose pulp by exposing the microbial cellulose pulp to a sodium hydroxide solution takes place for a period of less than 6 hours. Preferably still, the step of mercerizing the microbial cellulose pulp by exposing the microbial cellulose pulp to a sodium hydroxide solution takes place for a period of less than 3 hours.

Method for Producing a Viscose Dope from Microbial Cellulose

In a highly preferred form of the invention, the microbial cellulose pulp is suitable for the production of a viscose dope suitable for the production of viscose rayon fibres.

In a highly preferred form of the invention, the microbial cellulose pulp is suitable for the production of a viscose dope suitable for the cellulose sheeting.

In one form of the invention, after the step of mercerizing the microbial cellulose pulp, the method of the present invention comprises the step of:
    pressing the mixture of sodium hydroxide and microbial cellulose pulp to remove a portion of the sodium hydroxide solution.

In a preferred form of the present invention, the step of pressing the mixture of sodium hydroxide and microbial cellulose pulp to remove a portion of the sodium hydroxide solution, more specifically comprises:
    pressing the mixture of sodium hydroxide and microbial cellulose pulp to remove a portion of the sodium hydroxide solution, to a press factor of at least 3.

The press factor is a measure of the cellulose and sodium hydroxide content in the mixture of mercerised microbial cellulose pulp and sodium hydroxide solution after the pressing step. The press factor is calculated by dividing the weight of the cake after pressing with the weight of the original dry cellulose.

Where the press factor is at least 3, in a preferred form of the invention, the press factor is between 3 and about 6. Preferably still, the press factor is between 3 and about 4.5. Preferably still, the press factor is between 3 and about 4.

Where the press factor is at least 3, preferably the press factor is between 3 and 6. Preferably still, the press factor is between 3 and 4.5. Preferably still, the press factor is between 3 and 4.

In the context of the production of viscose dope from cellulose sourced from wood pulp, it is widely understood that press factors considerably lower than the press factors of the methods of the present invention are highly desirable in the production of viscose dopes appropriate for the production of viscose rayon fibres. The inventors have discovered that the mercerized microbial cellulose pulp produced in the context of the method of present invention is practically incapable of being pressed to the extent necessary to provide the press factors understood to be necessary for the generation of acceptable viscose dope from wood-pulp derived cellulose.

In one form of the present invention, following the step of pressing the mixture of sodium hydroxide and microbial cellulose pulp to remove a portion of the sodium hydroxide solution, the mixture of sodium hydroxide and microbial cellulose pulp comprises between 10 and 21 wt/wt % sodium hydroxide. Preferably, the mixture of sodium hydroxide and microbial cellulose pulp comprises between 11 and 20 wt/wt % sodium hydroxide. Preferably, the mixture of sodium hydroxide and microbial cellulose pulp comprises between 12 and 19 wt/wt % sodium hydroxide. Preferably, the mixture of sodium hydroxide and microbial cellulose pulp comprises between 13 and 18 wt/wt % sodium hydroxide. Preferably, the mixture of sodium hydroxide and microbial cellulose pulp comprises between 14 and 17 wt/wt % sodium hydroxide. Preferably, the mixture of sodium hydroxide and microbial cellulose pulp comprises between 15 and 16 wt/wt % sodium hydroxide. Preferably, the mixture of sodium hydroxide and microbial cellulose pulp comprises 15.5 wt/wt % sodium hydroxide.

Surprisingly, the inventors have discovered that acceptable viscose dope can be produced from microbial cellulose where the press factor is considerably higher than those required for wood pulp-derived cellulose.

In a preferred form of the invention, after the step of mercerizing the microbial cellulose pulp, the method comprises the steps of:
    treating the mercerised microbial cellulose pulp with carbon disulphide to produce a microbial cellulose xanthate.

Preferably still, the step of treating the mercerised microbial cellulose pulp with carbon disulphide to produce a microbial cellulose xanthate occurs after the step of pressing the mixture of mercerised microbial cellulose pulp and sodium hydroxide solution to remove a portion of the sodium hydroxide solution. Preferably still, the microbial cellulose pulp microbial cellulose pulp has a sodium hydroxide concentration of between 10 and 21 wt/wt %.

In a preferred form of the invention, the step of treating the mercerised microbial cellulose pulp with carbon disulphide to produce a microbial cellulose xanthate comprises the step of:
    treating the mercerised microbial cellulose pulp with carbon disulphide such that the concentration of the carbon disulphide is between 20 and 50% (w/w) of the dry weight of the microbial cellulose to produce a microbial cellulose xanthate.

In a preferred form of the invention, the concentration of the carbon disulphide is between 25 and 45% (w/w); preferably still between 30 and 40% (w/w). In a specific form of the invention, the concentration of the carbon disulphide is 36%.

In a preferred form of the invention, the step of treating the mercerised microbial cellulose pulp with carbon disulphide to produce a microbial cellulose xanthate comprises the step of:
    treating the mercerised microbial cellulose pulp with carbon disulphide to produce a microbial cellulose xanthate.

The present invention encompasses microbial cellulose xanthates produced by the methods of the present invention.

Preferably still the step of treating the mercerised microbial cellulose pulp with carbon disulphide to produce a microbial cellulose xanthate takes place at a temperature between at a temperature between about 5 and about 50° C.; preferably still about 5 and about 40° C.; preferably still a temperature between about 10 and about 40° C. Preferably still the step of treating the mercerised microbial cellulose pulp with carbon disulphide to produce a microbial cellulose xanthate takes place at a temperature between at a temperature between about 25 and about 35° C. Preferably still the step of treating the mercerised microbial cellulose pulp with carbon disulphide to produce a microbial cellulose xanthate takes place at a temperature between at a temperature between 5 and 50° C.; preferably still 5 and 40° C.; preferably still a temperature between 10 and 40° C.

Where the step of treating the mercerised microbial cellulose pulp with carbon disulphide to produce a microbial cellulose xanthate tales place at a temperature of between at a temperature between 5 and 50° C., in a preferred form of the invention, the step of treating the mercerised microbial cellulose pulp with carbon disulphide to produce a microbial cellulose xanthate takes place for a period of less than 90 minutes.

Preferably still, the step of treating the mercerised microbial cellulose pulp with carbon disulphide to produce a microbial cellulose xanthate takes place for a period of between 30 and 90 minutes.

In a preferred form of the invention, where the method comprises the step of treating the mercerised microbial cellulose pulp with carbon disulphide to produce a microbial cellulose xanthate, prior to the step of treating the mercerised microbial cellulose pulp with carbon disulphide to produce a microbial cellulose xanthate, the method further comprises the step of:
aging the mercerised microbial cellulose pulp.

In a preferred form of the invention, the step of aging the mercerised microbial cellulose pulp takes place for a period of between 0 and 10 hours. Preferably still, the step of aging the mercerised microbial cellulose pulp takes place for a period of between 1 and 5 hours. In a highly preferred form of the invention, the step of aging the mercerised microbial cellulose pulp takes place for a period of between about 60 and about 400 minutes. In a highly preferred form of the invention, the step of aging the mercerised microbial cellulose pulp takes place for a period of between 120 and 300 minutes.

In a preferred form of the invention, the step of aging the mercerised microbial cellulose pulp takes place for a sufficient period to reach a target dope viscosity of at least 150 ml/g. In one form of the present invention, the step of aging the mercerised microbial cellulose pulp takes place for a sufficient period to reach a target dope viscosity of at least 160 ml/g. In one form of the present invention, the step of aging the mercerised microbial cellulose pulp takes place for a sufficient period to reach a target dope viscosity of at least 170 ml/g. In one form of the present invention, the step of aging the mercerised microbial cellulose pulp takes place for a sufficient period to reach a target dope viscosity of at least 180 ml/g. In one form of the present invention, the step of aging the mercerised microbial cellulose pulp takes place for a sufficient period to reach a target dope viscosity of at least 190 ml/g. In one form of the present invention, the step of aging the mercerised microbial cellulose pulp takes place for a sufficient period to reach a target dope viscosity of at least 200 ml/g. In one form of the present invention, the step of aging the mercerised microbial cellulose pulp takes place for a sufficient period to reach a target dope viscosity of at least 210 ml/g. In one form of the present invention, the step of aging the mercerised microbial cellulose pulp takes place for a sufficient period to reach a target dope viscosity of at least 220 ml/g. In one form of the present invention, the step of aging the mercerised microbial cellulose pulp takes place for a sufficient period to reach a target dope viscosity of at least 230 ml/g. In one form of the present invention, the step of aging the mercerised microbial cellulose pulp takes place for a sufficient period to reach a target dope viscosity of at least 240 ml/g. In one form of the present invention, the step of aging the mercerised microbial cellulose pulp takes place for a sufficient period to reach a target dope viscosity of at least 250 ml/g.

The inventors have discovered that the accepted models for indicating appropriate aging times for mercerised cellulose pulps prior to xanthation for the purpose of producing a viscose dope indicate much higher aging times than the inventors have discovered are appropriate for the microbial cellulose-derived mercerised cellulose pulps of the invention.

In a preferred form of the invention, after the step of treating the mercerised microbial cellulose pulp with carbon disulphide to produce a microbial cellulose xanthate, the method comprises the step of:
dissolving the microbial cellulose xanthate.

In a preferred form of the invention, the step of dissolving the microbial cellulose xanthate to produce the viscose dope comprises the step of:
contacting the microbial cellulose xanthate with an aqueous solution of sodium hydroxide to produce a microbial cellulose viscose dope.

In a preferred form of the invention, the concentration of sodium hydroxide in the aqueous solution of sodium hydroxide is between 1 and 7%. In a preferred form of the invention, the concentration of sodium hydroxide in the aqueous solution of sodium hydroxide is between 3 and 6%. In a preferred form of the invention, the concentration of sodium hydroxide in the aqueous solution of sodium hydroxide is between 4 and 6%. Preferably the concentration of sodium hydroxide in the aqueous solution of sodium hydroxide is about 5%. Preferably the concentration of sodium hydroxide in the aqueous solution of sodium hydroxide is 5%.

In a preferred form of the invention, the step of contacting the microbial cellulose xanthate with an aqueous solution of sodium hydroxide to produce a microbial cellulose viscose dope takes place at depressed temperatures.

Preferably the step of contacting the microbial cellulose xanthate with an aqueous solution of sodium hydroxide to produce a microbial cellulose viscose dope takes place at a temperature of between about 0 and about 20° C. Preferably the step of contacting the microbial cellulose xanthate with an aqueous solution of sodium hydroxide to produce a microbial cellulose viscose dope takes place at a temperature of between about 5 and about 10° C. In a highly preferred form of the invention, the step of contacting the microbial cellulose xanthate with an aqueous solution of sodium hydroxide to produce a microbial cellulose viscose dope takes place at about 7° C.

Preferably the step of contacting the microbial cellulose xanthate with an aqueous solution of sodium hydroxide to produce a microbial cellulose viscose dope takes place at a temperature of between 0 and 15° C. Preferably the step of contacting the microbial cellulose xanthate with an aqueous solution of sodium hydroxide to produce a microbial cellulose viscose dope takes place at a temperature of between 5 and 10° C. In a highly preferred form of the invention, the step of contacting the microbial cellulose xanthate with an aqueous solution of sodium hydroxide to produce a microbial cellulose viscose dope takes place at 7° C.

In an alternative form of the present invention, the initial temperature of temperature of the step of contacting the microbial cellulose xanthate with an aqueous solution of sodium hydroxide is controlled. Preferably, the temperature of the solution is allowed to drift to ambient temperature throughout the step. Preferably the step of contacting the microbial cellulose xanthate with an aqueous solution of sodium hydroxide to produce a microbial cellulose viscose dope takes place at an initial temperature of between 0 and 30° C. The inventors have discovered that the microbial cellulose xanthates of the present invention are considerably slower-dissolving than cellulose xanthates produced from cellulose-pulps derived from wood. For example, under comparable conditions, cellulose xanthates produced from cellulose-pulps derived from wood would be expected to dissolve in approximately half the time observed for the microbial cellulose xanthates of the invention.

As would be understood by persons skilled in the art, when dissolving cellulose xanthates produced from cellulose-pulps derived from wood, any particles that have not dissolved after approximately 2 to 3 hours of contact with an aqueous solution of sodium hydroxide are unlikely to dissolve. The inventors have found that by conducting the step of contacting the microbial cellulose xanthate with an aqueous solution of sodium hydroxide for a period longer than that typically used for dissolving xanthates produced from cellulose-pulps derived from wood, the greater the extent of dissolution of particles.

In a preferred form of the invention, the step of contacting the microbial cellulose xanthate with an aqueous solution of sodium hydroxide takes place for a period of greater than 3 hours. In a preferred form of the invention, the step of contacting the microbial cellulose xanthate with an aqueous solution of sodium hydroxide takes place for a period of greater than 4 hours. In a preferred form of the invention, the step of contacting the microbial cellulose xanthate with an aqueous solution of sodium hydroxide takes place for a period of greater than 5 hours. In a preferred form of the invention, the step of contacting the microbial cellulose xanthate with an aqueous solution of sodium hydroxide takes place for a period of greater than 6 hours. In a preferred form of the invention, the step of contacting the microbial cellulose xanthate with an aqueous solution of sodium hydroxide takes place for a period of greater than 7 hours. In a preferred form of the invention, the step of contacting the microbial cellulose xanthate with an aqueous solution of sodium hydroxide takes place for a period of greater than 8 hours. In a preferred form of the invention, the step of contacting the microbial cellulose xanthate with an aqueous solution of sodium hydroxide takes place for a period of greater than 9 hours. In a preferred form of the invention, the step of contacting the microbial cellulose xanthate with an aqueous solution of sodium hydroxide takes place for a period of greater than 10 hours. In a preferred form of the invention, the step of contacting the microbial cellulose xanthate with an aqueous solution of sodium hydroxide takes place for a period of greater than 11 hours. In a preferred form of the invention, the step of contacting the microbial cellulose xanthate with an aqueous solution of sodium hydroxide takes place for a period of greater than 12 hours. In a preferred form of the invention, the step of contacting the microbial cellulose xanthate with an aqueous solution of sodium hydroxide takes place for a period of greater than 13 hours. In a preferred form of the invention, the step of contacting the microbial cellulose xanthate with an aqueous solution of sodium hydroxide takes place for a period of greater than 14 hours. In a preferred form of the invention, the step of contacting the microbial cellulose xanthate with an aqueous solution of sodium hydroxide takes place for a period of greater than 15 hours. In a preferred form of the invention, the step of contacting the microbial cellulose xanthate with an aqueous solution of sodium hydroxide takes place for a period of greater than 16 hours. In a preferred form of the invention, the step of contacting the microbial cellulose xanthate with an aqueous solution of sodium hydroxide takes place for a period of greater than 17 hours.

In a preferred form of the invention, the step of contacting the microbial cellulose xanthate with an aqueous solution of sodium hydroxide takes place for a period of between about 3.5 hours and about 18 hours. In a preferred form of the invention, the step of contacting the microbial cellulose xanthate with an aqueous solution of sodium hydroxide takes place for a period of between about 4 hours and about 15 hours. In a preferred form of the invention, the step of contacting the microbial cellulose xanthate with an aqueous solution of sodium hydroxide takes place for a period of between about 5 hours and about 10 hours. In a preferred form of the invention, the step of contacting the microbial cellulose xanthate with an aqueous solution of sodium hydroxide takes place for a period of between about 6 hours and about 8 hours.

In a preferred form of the invention, the step of contacting the microbial cellulose xanthate with an aqueous solution of sodium hydroxide takes place for a period of between 3.5 hours and 18 hours. In a preferred form of the invention, the step of contacting the microbial cellulose xanthate with an aqueous solution of sodium hydroxide takes place for a period of between 4 hours and 15 hours. In a preferred form of the invention, the step of contacting the microbial cellulose xanthate with an aqueous solution of sodium hydroxide takes place for a period of between 5 hours and 10 hours. In a preferred form of the invention, the step of contacting the microbial cellulose xanthate with an aqueous solution of sodium hydroxide takes place for a period of between 6 hours and 8 hours.

In a preferred form of the invention, agitation is provided to the solution during the step of contacting the microbial cellulose xanthate with an aqueous solution of sodium hydroxide. Preferably, the solution is stirred during the step of contacting the microbial cellulose xanthate with an aqueous solution of sodium hydroxide.

In a preferred form of the invention, after the step of contacting the microbial cellulose xanthate with an aqueous solution of sodium hydroxide to produce a microbial cellulose viscose dope the method comprises the step of:
ripening the microbial cellulose viscose dope.

As would be understood by a person skilled in the art, the degree of re-xanthation and the evenness of xanthation (viscose ripening) are measured by determining the concentration of salt solution required to precipitate the xanthate from viscose, typically by way of the salt figure test (which uses sodium chloride) and the Hottenroth test (which uses ammonium chloride), details for which are provided in Sengupta A K Rayon Fibres, in Gupta V B, Kothari V K editor, Manufactured Fibre Technology, $2^{nd}$ Ed., Springer Science and Business Media; 2012, p 580-513, the contents of which are incorporated by reference.

In a preferred form of the invention, the step of ripening the microbial cellulose viscose dope takes place at ambient temperature. In a preferred form of the invention, the step of ripening the microbial cellulose viscose dope takes place at a temperature between at a temperature between about 5 and about 50° C.; preferably still about 5 and about 40° C.; preferably still a temperature between about 10 and about 40° C.

In a preferred form of the invention, the step of ripening the microbial cellulose viscose dope takes place at ambient temperature. In a preferred form of the invention, the step of ripening the microbial cellulose viscose dope takes place at a temperature between at a temperature between 5 and 50° C.; preferably still 5 and 40° C.; preferably still a temperature between 10 and 40° C.

In one form of the present invention, the agitation is provided to the solution during at least a portion of the step of ripening the microbial cellulose viscose dope. Preferably, the solution is stirred during at least a portion of the step of ripening the microbial cellulose viscose dope. It is understood by the inventors that some settling of the dope may be required once the agitation has been stopped.

In certain forms of the invention, the method for producing a microbial cellulose viscose dope comprises the step of filtering the microbial cellulose viscose dope.

Methods for Producing a Microbial Cellulose Pulp

As noted above, the microbial cellulose pulp is produced by a method comprising the step of:
  exposing a microbial cellulose to a volume of water to form the microbial cellulose pulp for production of viscose dope, wherein the cellulose concentration in the microbial cellulose pulp is less than 0.040 g of cellulose per mL of pulp.

As noted above, the inventors have observed that in concentrations above 0.040 g of cellulose per mL of pulp, microbial cellulose exhibits physical properties that are undesirable for handling and, most importantly, prevent adequate mercerisation of the cellulose pulp using commercially practical methods. In particular, aggregation of the cellulose prevents adequate exposure of the cellulose to the sodium hydroxide solution necessary for the mercerisation necessary for the production of viscose dope.

The inventors have found that pulps with concentrations in excess of 0.040 g of cellulose per mL are not amenable to adequate mercerisation using commercial techniques.

In one form of the invention, cellulose concentration in the microbial cellulose pulp is greater than 0.001 g of cellulose per mL of pulp. While lower concentrations such as this do not attract the undesirable physical properties mentioned above, low concentrations are generally undesirable, as they involve handling larger volumes of liquids. The inventors consider that cellulose concentration in the microbial cellulose pulp is less than 0.001 g of cellulose per mL of pulp are unlikely to be commercially practical.

In a preferred form of the invention, the step of exposing a microbial cellulose to a volume of water to form the microbial cellulose pulp takes place at ambient temperature.

In a preferred form of the invention, the step of exposing a microbial cellulose to a volume of water to form the microbial cellulose pulp takes place at a temperature between about 5 and about 50° C.; preferably still a temperature between about 5 and about 40° C.; preferably still a temperature between about 10 and about 40° C.

In a preferred form of the invention, the step of exposing a microbial cellulose to a volume of water to form the microbial cellulose pulp takes place at a temperature between 5 and 50° C.; preferably still a temperature between 5 and 40° C.; preferably still a temperature between 10 and 40° C.

Conventional cellulose sources, such as wood pulp and cotton linters, contain hemicellulose and lignin, which must be removed, such as by the Kraft process. The inventors have discovered that microbial cellulose is essentially free of these contaminants, rendering Kraft-like processes unnecessary.

In one form of the invention, prior to the step of exposing a microbial cellulose to a volume of water to form the microbial cellulose pulp, the method for producing a microbial cellulose pulp of the present invention comprises the step of:
  washing the microbial cellulose with a cleaning agent.

In embodiments of the invention cleaning agent may be a detergent, such as an alkylbenzene sulfonate detergent, a quaternary ammonium detergent, a polyoxyethylene detergent, or a glycoside detergent.

In embodiments of the invention, the cleaning agent may be a bleaching agent, such as a chlorine, ozone, sodium hypochlorite or hydrogen peroxide.

In embodiments of the invention, the cleaning agent may be a caustic agent, such as sodium, potassium or calcium hydroxides or oxides.

In embodiment of the invention, the cleaning agent may be an anionic surfactant. Preferably, the anionic surfactant is selected from the group comprising sulfonic acid salts; alcohol sulfates; fatty alcohol sulfates; fatty alcohol ether sulfates; alkylbenzene sulfonates, phosphoric acid esters; carboxylic acid salts and mixtures thereof. In one form of the invention, the cleaning agent is Texapon® (BASF SE)

In embodiment of the invention, the cleaning agent may be a non-ionic surfactant. Preferably, the non-ionic surfactant is selected from the group comprising ethoxylates; fatty alcohol ethoxylates; alkylphenol ethoxylates; fatty acid ethoxylates; special ethoxylated fatty esters and oils; ethoxylated amines and/or fatty acid amides; terminally blocked ethoxylates; fatty acid esters of polyhydroxy compounds; fatty acid esters of glycerol; fatty acid esters of sorbitol; fatty acid esters of sucrose; alkyl polyglucosides; amine oxides; sulfoxides; and phosphine oxides. More preferably, the non-ionic surfactant is a fatty acid ester of sorbitol, such as Polysorbate 80 (Tween 80®, Sigma-Aldrich, Inc).

In a preferred form of the present invention, the cleaning agent is an aqueous solution comprising between 0.1% and 4% of a non-ionic surfactant. More preferably, the cleaning agent is an aqueous solution comprising between 0.5% and 2% of a non-ionic surfactant. More preferably, the cleaning agent is an aqueous solution comprising about 1% of a non-ionic surfactant.

In a preferred form of the present invention, the cleaning agent is an aqueous solution comprising between 0.1% and 4% of a fatty acid ester of sorbitol. More preferably, the cleaning agent is an aqueous solution comprising between 0.5% and 2% of a fatty acid ester of sorbitol. More preferably, the cleaning agent is an aqueous solution comprising about 1% of a fatty acid ester of sorbitol.

The invention encompasses the use of a single cleaning agent alone, or two or more cleaning agents in combination.

In embodiments of the present invention, the cleaning agent comprises a combination of a caustic agent and a non-ionic surfactant. More preferably, the caustic agent is sodium hydroxide and the non-ionic surfactant is a fatty acid ester of sorbitol. More preferably, the fatty acid ester of sorbitol is Polysorbate 80.

In a preferred form of the invention, the cleaning agent comprises between 0.5% and 3% sodium hydroxide and 0.1% and 4% non-ionic surfactant. More preferably, the cleaning agent comprises between 1% and 2% sodium hydroxide and 0.5% and 2% non-ionic surfactant. More preferably, the cleaning agent comprises about 1.5% sodium hydroxide and about 1% non-ionic surfactant.

In a preferred form of the invention, the cleaning agent comprises between 0.5% and 3% sodium hydroxide and 0.1% and 4% Polysorbate 80. More preferably, the cleaning agent comprises between 1% and 2% sodium hydroxide and 0.5% and 2% Polysorbate 80. More preferably, the cleaning agent comprises about 1.5% sodium hydroxide and about 1% Polysorbate 80.

As would be understood by persons skilled in the art, microbial cellulose may be derived from a range of sources, and may be contaminated by a range of inorganic or organic compounds (including residual bacterial cell debris, lipids/fats, proteins, carbohydrates, acetic acid, and residual culture media), which may interfere with the production of the viscose dope. Where the microbial cellulose is so contaminated, the detergent wash is advantageous. However, microbial cellulose can be produced in such a manner that it is contaminant-free, in which case the cleaning agent is unnecessary. This represents an advantageous embodiment of the present invention.

In a preferred form of the invention, where the method comprises the step of washing the microbial cellulose with a detergent, after the step of washing the microbial cellulose with a detergent, the method preferably comprises the step of:

washing the microbial cellulose with water.

The step of washing the microbial cellulose with water is intended to remove the cleaning agent. If no cleaning agent is used, advantageous forms of the invention do not comprise the step of washing the microbial cellulose with water. The step of washing the microbial cellulose with water may be performed multiples times. In preferred forms of the invention the step of washing the microbial cellulose with water may be performed twice.

In a highly preferred form of the invention, prior to the step of exposing a microbial cellulose to a volume of water to form the microbial cellulose pulp, the method of the present invention comprises the step of:

subdividing the microbial cellulose.

In a highly preferred form of the invention, the step of subdividing the microbial cellulose takes place before any step of washing the microbial cellulose with a cleaning agent.

In a highly preferred form of the invention, the method for producing a microbial cellulose pulp of the present invention comprises the steps of:

exposing the microbial cellulose to a volume of water to form the microbial cellulose pulp for production of viscose dope, wherein the cellulose concentration in the microbial cellulose pulp is less than 0.040 g of cellulose per mL of pulp; and homogenising the microbial cellulose pulp such that the particle size distribution of the pulp has a D90 less than 1700 µm. The present invention encompasses microbial cellulose pulps produced by the herein described methods of the present invention.

Conventional techniques for the preparation of cellulose pulp from wood pulp for the production of viscose dope entail heating the cellulose source while exposing the cellulose source to certain reagents. As preferred forms of the present invention comprise exposing microbial cellulose to water at ambient temperature, these forms consume considerably less energy than conventional approaches.

As noted above, the use of a detergent in the method of the present invention is optional. Embodiments of the invention where no detergent is used afford a distinct environmental and input cost advantage over conventional techniques for the preparation of cellulose pulp from wood pulp. These conventional techniques employ extensive quantities of sodium hydroxide and/or sodium sulphide, both of which attract considerable environmental and cost overhead. As such, these forms of the invention provide considerable advantage over conventional techniques.

Methods for Producing Articles of Manufacture

The present invention encompasses viscose dopes produced by the methods of the present invention.

The present invention encompasses articles of manufacture produced using the viscose dope of the present invention including, but not limited to, viscose rayon fibres and viscose sheeting.

In a preferred form of the invention, the viscose dope has a Mw of between about 100 000 and 200 000 gmol$^{-1}$.

In a preferred form of the invention, the viscose dope has a cellulose content of between about 9 and 10% (w/w).

In a preferred form of the invention, the viscose dope has a filter clogging value of between 50 and 80.

In a preferred form of the invention, the viscose dope has a ripening index of between 5 and 15. Preferably still the viscose dope has a ripening index of between 5 and 13. Preferably still the viscose dope has a ripening index of between 5 and 12. Preferably still the viscose dope has a ripening index of between 5 and 11. Preferably still the viscose dope has a ripening index of between 5 and 10.

The filter clogging value is determined by the Trieber method (see "Chemical Changes of Cellulose Pulps In the Processing of Viscose to Dope" Strunk P, Lindgren A, Eliasson B, Agnemo R. 2012; 46(9-10): 559-569, the contents of which are incorporated by reference), and is calculated by the following formula:

$$Kw = \frac{2 \times \left[\frac{t2}{M2} - \frac{t1}{M1}\right] \times 10^5}{t2 - t1}$$

Where t1, t2 are the filtration time in min (at 20 and 60 min) respectively, M1 and M2 are the mass of viscose dope in grams filtered during 0-20 min and 0-60 min respectively.

Once the filter clogging value is calculated it is then adjusted for viscosity, $K_r$:

$$Kr = \frac{Kw}{\eta^{0.4}}$$

where $\eta$ is the ball time in seconds.

Viscose Rayon Fibre

In a preferred form of the invention, the viscose dope is suitable for producing a viscose rayon fibre.

Methods for the production of viscose fibres are known to persons skilled in the art. See, for example Wilkes, Andrew, 2001, "The Viscose Process", "In Regenerated Cellulose Fibres", edited by Calvin Woodings, p 37-61, Cambridge: Woodhead Publishing Ltd, the contents of which are incorporated by reference.

Viscose dope is typically filtered just before spinning, as there will typically be some particulate matter present in the viscose dope. Removing the particulate material, no matter how minute or insignificant, will prevent blockage of the holes in the spinning jet. Historically, cloth filters were employed in filter presses to remove particulates, with typically a three stages of filtration, each stage consisting of a number of plate and frame units in parallel. Once covered by particulates, cloths would be removed manually and washed for re-use or discarded. It is believed to be important to establish a reasonable residence time for the viscose between each stage of filtration in order to achieve maximum particulate removal efficiencies. Most modern viscose plants now favour the use of automatic mechanical filters. These essentially consist of sintered metal screens with hole sizes in the 10-30 μm range. Mechanical filters can also allow certain materials to pass through, particulate fibres which in cross-section are smaller than the sinter hole size. Further filtration is sometimes effected at the spinning machines, whether by central filters on each spinning line, by candle filters on each spinning rounder arm and/or by filter cloths in each jet assembly.

The porosity of the filters depends on the spinning system. For example to spin viscose dope through a spinning system that has 80 μm holes then the dope will be filtered through ~30 μm prior to spinning. If the spinning system has bigger holes then the filtration can be more porous accordingly. The spinning system depends on the type of fibre/product to be regenerated. For staple fibres, fibres are regenerated through 50-80 μm holes.

The viscose dopes of the present invention are filterable through 5 μm polytetrafluorethylene (PTFE) syringe filter (resist syringe filter). This syringe filter is made for viscous liquids. Although this filtration method is different to the typical industrial process (mechanical or cloth filtration as described above), the inventors consider that it is an appropriate indicia of performance of the viscose dopes of the present invention for the purpose of producing viscose rayon fibres in that if the viscose dope is filterable through 5 μm, then it can reasonably be assumed that it is filterable through filters with greater pore size.

As would be understood by a person skilled in the art, the ability of a viscose dope to be filtered is described as "filterability". If a viscose dope generated from traditional sources of cellulose (such as wood pulp and cotton linters) cannot be filtered under pressure (vacuum and press) within ~30 minutes then the dope is generally considered unfilterable. This is because the dope becomes less fluid-like and more gel-like at room temperature with time, potentially rendering it unsuitable for spinning. Observations for viscose dopes of the present invention show dope is stable for longer times at room temperature.

To ensure continuity at spinning, the viscose must be deaerated to remove any dispersed air or other gases that might otherwise cause small bubbles to form as the viscose is extruded into filament form through the jet. Traditional techniques is where a vacuum is applied while the viscose is passed over a surface to maximise its surface: volume ratio. There are "cone", "film" and "tank" deaerators. Note some water and $CS_2$ is lost from the viscose at deaeration.

After regeneration of the fibres the fibre is contaminated with sulfuric acid, zinc sulfate, hydrogen sulfide and carbon disulfde (and small amounts of sulfur and polysulfides), and must be washed. Commonly, washing is achieved by having a multistate counter-current machine. For example a moving rail, flat bed or tank immersion type. Generally, washing comprises multiple phases:

1. Acid water wash (also known as hot water wash), which is typically carried at 90° C. in sulfuric acid solution to complete regeneration and vaporise regeneration products ($H_2S$ and $CS_2$);
2. Desulfurisation to dissolve any sulfur or residual polysulfides (and neutralise residual acid) by washing in $NaOH/Na_2S$ or NaSH at 60° C., pH at 11-12;
3. Water wash;
4. Bleaching with hydrogen peroxide or ozone (for "totally chlorine free products") or sodium hypochlorite;
5. Water wash To remove residual bleaching agent;
6. Optionally, a small amount of acid may be added to correct fibre pH and convert any residual zinc to a soluble form.

In almost all commercial cases viscose fibres are finished with a processing lubricant prior to drying and baling. The choice of lubricant depends on end-use requirements. Common lubricants used are fatty acids, salts of fatty acids, ethoxylated fatty acids and ethers. See, for example, The Glycerine Producers' Association. Uses Of Glycerine; and Wilkes A G. The Viscose Process. In: Woodings C, editor. Regenerated Cellulose Fibres. 1st ed. Cambridge (UK): Woodhead Publishing Limited; 2001. p. 37-61, the contents of which are incorporated by reference.

In one aspect, the invention comprises a method for making a viscose rayon fibre from the microbial cellulose viscose dope of the invention.

The present invention includes viscose rayon fibres produced by such methods.

Viscose Sheets

In a preferred form of the invention, the viscose dope is suitable for producing a viscose sheet.

Methods for the production of viscose sheets are known to persons skilled in the art.

Viscose is extruded under pressure upon a smooth surface of a moving roller and transferred at uniform thickness into a coagulating bath (sulfuric acid, zinc sulfate and sodium sulfate) regenerating a film of cellulose, which is then stripped from the roll onto another in a continuous manner through a series of vats. The regenerated cellulose film is passed through vats to wash as described above in the context of the productions of viscose rayon fibres.

In addition the washed regenerated cellulose film is passed through a glycerine solution of high purity and then dried. The "film" or "cellophane" retains between 10 and 25 percent of its weight of glycerine, which imparts flexibility and durability to the finished and product and reduces shrinkage.

See, for example, see Branderberger J E, Manufacture of Viscose Films, U.S. Pat. No. 1,548,864. 1925 Aug. 11; Hyden W. Manufacture and Properties of Regenerated Cellulose Films. Industrial and Engineering Chemistry. 1925; 21(5): 405-410, and Branderberger J E, Apparatus For The Continuous Manufacture Of Cellulose Films. U.S. Pat. No. 991,267, the contents of each of which are incorporated by reference.

In one aspect, the invention comprises a method for making a viscose sheet from the microbial cellulose viscose dope of the invention.

The present invention includes a viscose sheet produced by such methods.

Microbial Cellulose

Microbial cellulose for use in the methods of the present invention can be produced by a variety of means well known in the art. For example:

Hestrin, S. & Schramm, M. (1954) Synthesis of cellulose by *Acetobacter xylinum*. 2. Preparation of freeze-dried cells capable of polymerizing glucose to cellulose. *Biochem. J.* 58 (345-352)

Czaja, W., Krystynowicza, A., Bieleckia, S. & Brown, R. M. Jr. (2006) Microbial cellulose—the natural power to heal wounds. Biomaterials 27 145-151

Czaja, W. K., Young D. J., Kawecki, M. & Brown R. M. Jr. (2007). The future prospects of microbial cellulose in biomedical applications. Biomacromolecules; 8(1):1-12

Mendes, P. N., Rahal, S. C., Marques Pereira-Jr, O. C., Fabris, V. E., Rahal Lenharo, S. L., Ferreira de Lima-Neto, J. & da Cruz Landim-Alvarenga, F. (2009) In vivo and in vitro evaluation of an *Acetobacter xylinum* synthesized microbial cellulose membrane intended for guided tissue repair. Acta Veterinaria Scandinavica, 51:12

Albert Mihranyan (2011) Cellulose from cladophorales green algae: From environmental problem to high-tech composite materials DOI: 10.1002/app.32959 Journal of Applied Polymer Science Volume 119, Issue 4, pages 2449-2460.

In a preferred form of the invention, the microbial cellulose is microbial cellulose produced by bacteria of the genus *Acetobacter*.

Bacteria of the genus *Acetobacter* can be readily identified by persons skilled in the art by the growth of colonies on a medium containing about 7% ethanol and enough calcium carbonate to render it partially opaque. When *Acetobacter* colonies form enough acetic acid from the ethanol, the calcium carbonate around the colonies dissolves, forming a very distinct clear zone.

Definitions

Throughout this specification, unless the context requires otherwise, the term "microbial cellulose", means cellulose produced by bacteria.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The invention described herein may include one or more range of values (e.g. size, displacement and field strength etc.). A range of values will be understood to include all values within the range, including the values defining the range, and values adjacent to the range which lead to the same or substantially the same outcome as the values immediately adjacent to that value which defines the boundary to the range.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

EXPERIMENTS

Certain aspects of the present invention will now be demonstrated by a series of experiments. These experiments are intended to be illustrative of aspects of the present invention only, and should not be considered to in any way limit the generality of the foregoing description of the invention.

Materials and Methods

Size Exclusion Chromatography (SEC)—Mw

SEC is a type of liquid chromatography consisting of a solid stationary phase and a liquid mobile phase. It is a technique for measuring chain lengths of polymers by separating them on the basis of their size.

The instrumentation consists of a pump to push the solvent through the instrument, injection port to introduce the sample, a column to hold the 'stationary phase' and one or more detectors to detect the components as they leave the column. And lastly computation and software to calculate the results.

The polymer is first dissolved in a solvent. In this case the cellulose polymer is dissolved in a lithium chloride/dimethylacetamide (LiCl/DMAc) mix. When polymers are dissolved in solution they coil up on themselves as opposed to existing as 'linear' 'chains'. Hence in solution polymers exist as, and behave like tiny spheres. The size of the sphere is dependent on the molecular weight (i.e. large polymer→large sphere).

Once the polymer is dissolved in the solvent the solution is injected and flows through the column. The column matrix consists of the 'stationary phase' which in SEC is a porous structure of polymer beads. As the polymer solution moves down the column partitioning occurs repeatedly with diffusion acting to bring polymer molecules into and out of pores. Small polymers can enter many pores in the beads and thus take a long time to elute. Long polymers cannot enter many pores and thus move through the column quickly. Elution times are detected and recorded in a graph called a chromatogram. Higher molecular weights hence larger polymer 'coils' elute first, followed by successively lower molecular weight polymers (smaller polymer 'coils') emerging later.

Data produced on the chromatogram is then compared to the calibration (which shows the elution behaviour of a series of polymers of known molecular weights), and then the molecular weight distribution is calculated.

In the following description, molecular weight distribution analyses were determined on a PL-GPC 220 with RI-detector, with a mobile phase: 0.5% (w/v) LiCl/DMAc at a flow rate of 1 mL/min, at a temperature of 70° C., using 20 µm Mixed-A columns from Polymer Lab, arranged as one guard column and two 30 cm columns in series.

The method used is relative and the results can only be compared with samples analysed with the same method, column type and number of columns. In one form of the invention, the Mw parameters described above are as derived from measurement taken using the methodology described above. Methods for calculating the Mw are described in "An Introduction to Gel Permeation Chromatography and Size Exclusion Chromatography", Agilent Technologies, 2015, https://www.agilent.com/cs/library/primers/Public/5990-6969EN%20GPC%20SEC%20Chrom%20Guide.pdf, and "More S, Barth H G. Size Exclusion Chromatography", 1st ed. Berlin (Ger), Springer-Verlag Berlin and Heidelberg GmbH & Co. KG., 1999, p 234, the contents of both of which are incorporated by reference.

Particle Size Measurements

Particle Size Distribution was determined using the Mastersizer 2000 (Malvern, UK) laser diffractometer. The measurements were conducted using the dispersion unit 'Hydro 2000SM(A)'. The Hydro 2000SM is a wet sample dispersion unit which has a continuously variable single shaft pump and stirrer. In each measurement the amount of the sample pulp placed within the measurement system was such that the value of obscurance fell within the range of 10-20%. The speed of the pump and stirrer was selected so as to obtain maximum homogenization of the suspension. For pulps greater that 1.0 wt/wt % homogenization could not be achieved due to the thick gel nature of the sample and thus could not be measured. For all other samples that were measured the stirrer speed was set at 2000 r.p.m.

The intensity of the laser light registered on the particular detectors of the measurement system can be converted to particle size distribution according to the Mie Theory or the Fraunhofer theory. The choice of the theory is up to the performer of the measurements. The standard ISO 13320 recommends the application of the Mie Theory for particles smaller than 50 µm and for larger particles both theories provide similar results. The Fraunhofer model can predict the scattering pattern that is created when a solid, opaque disc of a known size is passed through a laser beam. However due to the sample nature very few particles are believed to be disc shaped and completely opaque and thus the Mie Theory was employed for measuring the particle size of the pulps. The Mie theory accurately predicts the light scattering behaviour of all materials under all conditions. The Mie Model predicts the way light is scattered through spherical particles and considers the way light passes through, or is absorbed by, the particle.

Therefore it is necessary to determine the values of the indices of absorption and refraction index of the sample. The refractive index was measured to be 1.33 (same as water, as the dispersion phase is water) and the absorption was assumed to be 0.01 (note that the absorption is usually based on the colour intensity of the sample. The lighter, more transparent the sample is observed, the lower the absorption value for example 0.0001).

The Mastersizer 2000 measures samples in triplicate and reports the values as an average. In regards to sample preparation, samples were diluted enough to avoid blockage and disruption of the dispersion unit. Note dilutions of a sample do not affect the particle size measurements. The % vol of samples can be found in the reports provided by the software of the instrument.

The instrument is calibrated using a standard provided by the manufacturer of the instrument (Malvern, UK); the standard is a polymer monosphere dispersion in water.

EXAMPLES OF THE INVENTION

Example 1

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 µm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%. The sheets are mechanically shredded into flakes ranging from 24 $mm^2$ to 100 $mm^2$.

Microbial cellulose sheet (5.0 g) was cut into 24 $mm^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The treated squares (5.0 g) were then isolated via a sieve and added to fresh water (1.0 L) and then boiled for 20 minutes. The mixture was cooled to room temperature and the squares were isolated via a sieve and added to deionised water (667 mL) and blended for 5 minutes using the 600 W Nutribullet with extractor blade to afford a homogenous thick white pulp (7.5 g $L^{-1}$, particle size: D10=25 µm, D50=129 µm, D90=502 µm, $M_w$=1,005,257, PD=3.8). Sodium hydroxide pellets (180 g, 4.50 mol) were added to deionised water (333 mL) and stirred in a cold water bath until the pellets dissolved. The microbial cellulose pulp (667 mL) was then added to the sodium hydroxide solution and the resulting mixture (cellulose concentration=4.8 $gL^{-1}$) vigorously stirred by magnetic stirring for 5 minutes at room temperature causing the resultant pulp to uniformly disperse. The reaction mixture was then heated and gently stirred at 50° C. for 2 hours before the hot reaction mixture was quickly vacuum filtered through a Buchner funnel to yield a wet off-white solid. The solid was then pressed between Whatman filter paper (grade 1) several times until no further liquid could be expressed before being transferred to a tared 250 mL two necked round bottom flask fitted with a rubber septum and gas adaptor with tap. The net weight of the solid was 20.7 g (press factor=4.1). The reaction vessel was evacuated via a vacuum pump and sealed from the outside atmosphere with the septum. Carbon disulfide (1.80 g, 1.42 mL, 0.0236 mol) was then introduced to the reaction flask through a septum via syringe which was then gently agitated before being allowed to stand in a water bath at 30-34° C. After 60 minutes the solid became bright orange and sticky where upon the septum was removed and the mixture was exposed to air for 1 minute. The flask was resealed with the septum and then immersed in an ice bath for 5 minutes. Sodium hydroxide solution (5.0%, 50 mL) was added to the orange solid with stirring at 0-5° C. After 6 hours the mixture changed from a sticky mass with suspended solids to a very thick, clear viscous orange liquid. The viscous liquid was then slowly stirred at ambient temperature for 16 hours giving a very viscous orange liquid; viscose dope (cellulose content=10% vol Hottenroth index=9, ball $fall_{10\ cm}$=192 seconds), clearly suitable for production of a viscose fibre.

Example 2

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp that was then passed through a deckle to form a wet solid sheet. The sheet was then freeze dried to afford a dry white sheet.

The freeze-dried sheet (1.052 g) was added to deionised water (130 mL) and blended for 1 minute using the 600 W Nutribullet with extractor blade to afford a homogenous thick white pulp (8.1 g L$^{-1}$, particle size: D10=72 μm, D50=408 μm, D90=1186 μm, M$_w$=1005257, PD=3.8). Sodium hydroxide pellets (36.037 g, 0.901 mol) were added to deionised water (70 mL) and stirred in a cold water bath until pellets dissolved. The microbial cellulose thick white pulp (130 mL) was then added to the this sodium hydroxide solution and the resulting mixture (cellulose concentration=5.1 g L$^{-1}$) was vigorously stirred by magnetic stirring for 5 minutes at room temperature causing the resultant pulp to uniformly disperse. The reaction mixture was then heated and gently stirred at 50-55° C. for 75 minutes before the hot reaction mixture was quickly vacuum filtered through a Buchner funnel to yield a wet off-white solid.

The solid was then pressed between dry Whatman filter paper (grade 1) several times until no further liquid could be expressed before being transferred to a tared 100 mL two necked fitted with a rubber septum and gas adapter with tap. The net weight of the solid was 4.83 g (press factor=4.6). The reaction vessel was evacuated via a vacuum pump and sealed from the outside atmosphere with the septum. Carbon disulfide (0.35 g, 0.28 mL, 4.6 mmol) was then introduced to the reaction flask through a septum via syringe which was then gently agitated before being allowed to stand in a water bath at 30-32° C. After 60 minutes the solid became bright orange and sticky where upon the septum was removed and the mixture was exposed to air for 5 minutes. The flask was resealed with the septum and then immersed in an ice bath for 5 minutes. Sodium hydroxide solution (5.0%, 10 mL) was added to the orange solid with stirring at 0-5° C. After 17 hours the mixture changed from a sticky mass to a homogenous thick viscous liquid; viscose dope (cellulose content=10% wt/vol, Hottenroth index=9, ball fall$_{10\ cm}$=192 seconds). The viscose dope was able to be filtered through a 5 μm PTFE syringe filter ("Rezist Syringe Filter"). Accordingly, the viscose dope would be expected to be suitable for spinning viscose rayon fibres.

Example 3

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp that was then passed through a deckle to form a wet solid sheet. The sheet was then freeze dried to afford a dry white sheet.

The dry microbial cellulose sheet (1.05 g) was added to deionised water (130 mL) and blended for 1 minute using a conventional blender to afford a homogenous thick white pulp (8.1 g L$^{-1}$, particle size: D10=72 μm, D50=408 μm, D90=1186 μm, M$_w$=1005257, PD=3.8).

Sodium hydroxide pellets (36.22 g, 0.906 mol) were added to deionised water (70 mL) and stirred in a cold water bath until pellets dissolved. The microbial cellulose thick white pulp (130 mL) was then added to the sodium hydroxide solution and the resulting mixture (cellulose concentration=5.1 g L$^{-1}$) was vigorously stirred by magnetic stirring for 5 minutes at room temperature causing the resultant pulp to uniformly disperse. The reaction mixture was then heated and gently stirred at 50-53° C. for 90 minutes before the hot reaction mixture was vacuum filtered through a Buchner funnel to yield a wet off-white solid which was left to stand on the funnel for 5 minutes. The solid was then pressed between dry Whatman filter paper (grade 1) several times until no further liquid could be expressed before being transferred to a tared 100 mL two necked round bottom flask fitted with a rubber septum and gas adaptor with tap. The net weight of the solid was 4.80 g (press factor=4.5). The reaction vessel was evacuated via a vacuum pump and sealed from the outside atmosphere with the septum. Carbon disulfide (0.35 g, 0.28 mL, 4.6 mmol) was introduced to the reaction flask through a septum via syringe which was then gently agitated before being allowed to stand in a water bath at 30-34° C. After 45 minutes the solid became orange in colour and sticky where upon the septum was removed and the mixture was exposed to air for 10 minutes. The flask was resealed with the septum and then immersed in an ice bath for 5 minutes. Sodium hydroxide solution (5.0%, 10 mL) was added to the orange solid with stirring at 0-5° C. After 1 hour the mixture changed from a sticky mass to a thick viscous orange liquid with some large gel-like particles. The resultant mixture was allowed to slowly stir at 10-16° C. to afford a viscous orange liquid with a few undissolved suspended white solids. The resultant mixture was then filtered through a 5 μm PTFE syringe filter ("Rezist Syringe Filter") to afford a clear viscous orange liquid; viscose dope (cellulose content=10% wt/vol).

Example 4

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was cut into 24 mm² squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp that was then passed through a deckle to form a wet solid sheet. The sheet was then freeze dried for one day to afford a dry white sheet.

The freeze-dried sheet (1.018 g) was added to deionised water (130 mL) and blended for 1 minute using the 600 W Nutribullet with extractor blade to afford a homogenous thick white pulp (7.8 g L$^{-1}$, particle size: D10=72 μm, D50=408 μm, D90=1186 μm, M$_w$=1005257, PD=3.8).

Sodium hydroxide pellets (36.189 g, 0.905 mol) were added to deionised water (70 mL) and stirred in a cold water bath until the pellets dissolved. The microbial cellulose thick white pulp (130 mL) was then added to this sodium hydroxide solution and the resulting mixture (cellulose concentration=4.9 g L$^{-1}$) was stirred by magnetic stirring at 50-55° C. for 85 minutes. The reaction mixture was then vacuum filtered through a Buchner funnel to yield a wet off-white solid. The solid was then pressed between dry Whatman filter paper (grade 1) several times until no further liquid could be expressed before being transferred to a tared 100 mL two necked round bottom flask fitted with a rubber septum and gas adaptor with tap and rested at room temperature for 2 hours. The net weight of the solid was 5.4 g (press factor=5.3). The reaction vessel was evacuated via a vacuum pump and carbon disulfide (0.35 g, 0.28 mL, 4.6 mmol) was introduced to the reaction flask through a septum via syringe which was then gently agitated before being allowed to stand in a water bath at 32° C. After 60 minutes the solid became bright orange and sticky where upon the septum was removed and the mixture was exposed to air for 5 minutes. The flask was resealed with the septum and then immersed in an ice bath for 5 minutes. Sodium hydroxide solution (5.0%, 10 mL) was added to the orange solid with stirring at 0-5° C. After 1 hour the mixture changed from a sticky mass to a homogenous thick viscous liquid with few clumps. The dissolving mixture was slowly stirred at ~16° C. for 17 hours to afford a thick viscous orange liquid; viscose dope (cellulose content=10% wt/vol). The viscose dope was filtered through a 5 μm PTFE syringe filter ("Rezist Syringe Filter").

Example 5

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

The microbial cellulose sheet (1.343 g) was dry-blended to a small particulate solid and then added to 18% sodium hydroxide solution (100 mL). The reaction mixture (cellulose concentration=13.4 g L$^{-1}$, 100 mL) was then heated and vigorously stirred at 50° C. for 2.3 hours before the hot reaction mixture was quickly vacuum filtered through a Buchner funnel to yield a wet off-white translucent solid. The solid was then transferred to a tared 100 mL two necked round bottom flask. The net weight of the solid was 1.423 g (press factor=1.06). The reaction vessel was sealed and then allowed to stand in a water bath at 50° C. for 19 hours. Carbon disulfide (0.44 g, 0.35 mL, 5.8 mmol) was then introduced to the reaction flask through a septum via syringe which was then gently agitated before being allowed to stand at ambient temperature. After 3 hours the solid became a gelatinous translucent pale orange solid where upon the septum was removed and the mixture was exposed to air for 1 minute. The flask was resealed with the septum and then immersed in an ice bath for 5 minutes. Sodium hydroxide solution (5.0%, 13.0 mL) was added to the orange solid with stirring at 0-5° C. After 1 hour the mixture remained unchanged and nothing of the solid appeared to have dissolved.

Example 6

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and dried in an oven at 105° C. The dried solid (1.034 g) was added to deionised water (103.5 mL) and blended for 5 minutes using the 600 W Nutribullet with extractor blade to afford a homogenous thick white pulp (10 g L$^{-1}$, M$_w$=1005257, PD=3.8). Sodium hydroxide pellets (36.022 g, 0.901 mol) were added to deionised water (100 mL) and stirred in a cold water bath until the pellets were dissolved. The microbial cellulose thick white pulp (103.5 mL) was then added to this sodium hydroxide solution and the resulting mixture (cellulose concentration=4.9 g L$^{-1}$) vigorously stirred by magnetic stirring for 5 minutes at room temperature causing the pulp to uniformly disperse. The reaction mixture was then heated and gently stirred at 50° C. for 2 hours before the hot reaction mixture was quickly vacuum filtered through a Buchner funnel to yield a wet off-white solid. The solid was then pressed between dry Whatman filter paper (grade 1) several times until no further liquid could be expressed before being transferred to a tared 100 mL two-necked round bottom flask fitted with a rubber septum and gas adaptor. The net weight of the solid was 4.33 g (press factor=4.1). The reaction vessel was evacuated via a vacuum pump and sealed from the outside atmosphere with a septum. Carbon disulfide (0.37 g, 0.29 mL, 4.8 mmol) was then introduced to the reaction flask through a septum via syringe which was then gently agitated before being allowed to stand in a water bath at 32° C. After 60 minutes the solid became bright orange and slightly sticky where upon the septum was removed and the mixture was exposed to air for 1 minute. The flask was resealed with the septum and then immersed in an ice bath for 5 minutes. Sodium hydroxide solution (5.0%, 10 mL) was added to the orange solid with stirring at 0-5° C. After 17 hours at ambient temperature the mixture was a brown viscous clear liquid; viscose dope (cellulose content=10% wt/vol).

Example 7

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was shredded into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and dried in an oven at 105° C. The dried solid (3.027 g) was added to deionised water (202 mL) and blended for 3 minutes using the 600 W Nutribullet with extractor blade to afford a homogenous thick white pulp (15 g L$^{-1}$, M$_w$=1005257, PD=3.8).

Sodium hydroxide pellets (36.086 g, 0.902 mol) were added to deionised water (100 mL) and stirred in a cold water bath until the pellets were dissolved. The microbial cellulose wet solid (100 mL) was then added to the sodium hydroxide solution and the resulting mixture (cellulose concentration=7.3 g L$^{-1}$) vigorously stirred by magnetic stirring for 5 minutes at room temperature causing the resultant pulp to uniformly disperse. The reaction mixture was then heated and magnetically stirred at 50° C. for 2 hours before the hot reaction mixture was quickly vacuum filtered through a Buchner funnel to yield a wet off-white solid. The solid was then pressed between dry Whatman filter paper (grade 1) several times until no further moisture could be expressed before being transferred to a tared 100 mL two necked round bottom flask. The net weight of the solid was 7.17 g (press factor=4.7). The reaction vessel was evacuated via pump and sealed from the outside atmosphere with a septum. Carbon disulfide (0.56 g, 0.44 mL, 7.3 mol) was then introduced to the reaction flask through a septum via syringe which was then gently agitated before being allowed to stand in a water bath at 32° C. After 60 minutes the solid became bright orange and slightly sticky where upon the septum was removed and the mixture was exposed to air for 1 minute. The flask was resealed with the septum and then immersed in an ice bath for 5 minutes. Sodium hydroxide solution (5.0%, 15 mL) was added to the orange solid with stirring at 0-5° C. After 17 hours at ambient temperature the mixture was a brown thick viscous liquid (cellulose content=10% wt/vol).

Example 8

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was shredded into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and dried in an oven at 105° C. The dried solid (3.057 g) was added to deionised water (202 mL) and blended for 5 minutes using the 300 W Braun Multiquick 1 Hand Processor to afford a homogenous thick white pulp (15 g L$^{-1}$, M$_w$=1005257, PD=3.8).

Sodium hydroxide pellets (54.06 g, 1.352 mol) were added to deionised water (200 mL) and stirred in a cold water bath until the pellets were dissolved. The microbial cellulose wet solid (100 mL) was then added to the sodium hydroxide solution and the resulting mixture (cellulose concentration=7.6 g L$^{-1}$) vigorously stirred by magnetic stirring for 5 minutes at room temperature causing the resultant pulp to uniformly disperse. The reaction mixture was then heated and magnetically stirred at 50° C. for 2 hours before the hot reaction mixture was quickly vacuum filtered through a Buchner funnel to yield a wet off-white solid. The solid was then pressed between dry Whatman filter paper (grade 1) several times before being transferred to a tared 100 mL round bottom flask. The net weight of the solid was 8.327 g (press factor=5.4). The reaction vessel was evacuated via pump and sealed from the outside atmosphere with a septum. Carbon disulfide (0.55 g, 0.43 mL, 7.2 mol) was then introduced to the reaction flask through a septum via syringe which was then gently agitated before being allowed to stand in a water bath at 32° C. After 55 minutes the solid became bright orange and slightly sticky where upon the septum was removed and the mixture was exposed to air for 1 minute. The flask was resealed with the septum and then immersed in an ice bath for 5 minutes. Sodium hydroxide solution (5.0%, 15 mL) was added to the orange solid with stirring at 0-7° C. After 17 hours at ambient temperature the mixture was a brown thick viscous clear liquid.

Example 9

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was shredded into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and dried in an oven at 105° C. The dried solid (3.02 g) was added to deionised water (100 mL) and blended for 3 minutes using the 300 W Braun Multiquick 1 Hand Processor to afford a thick wet solid mass (30 g L$^{-1}$, M$_w$=1005257, PD=3.8).

Sodium hydroxide pellets (17.988 g, 0.450 mol) were added to deionised water (50 mL) and stirred in a cold water bath until the pellets were dissolved. The microbial cellulose wet solid (51.167 g) was then added to the sodium hydroxide solution and the resulting mixture (cellulose concentration=15 g L$^{-1}$) was briefly vigorously stirred by hand and then heated and magnetically stirred at 50° C. for 103 minutes before the hot reaction mixture was vacuum filtered through a Buchner funnel to yield a moist off-white solid that consisted of some pale brown solids. The solid was then pressed between dry Whatman filter paper (grade 1) two times before being transferred to a tared 100 mL two necked round bottom flask. The net weight of the solid was 7.361 g (press factor=4.9). The reaction vessel was evacuated via pump and sealed from the outside atmosphere with a septum. Carbon disulfide (0.55 g, 0.43 mL, 7.2 mol) was then introduced to the reaction flask through a septum via syringe which was then gently agitated before being allowed to stand in a water bath at 32° C. After 55 minutes the solid became bright orange and slightly sticky where upon the septum was removed and the mixture was exposed to air for 1 minute. The flask was resealed with the septum and then immersed in an ice bath for 5 minutes. Sodium hydroxide solution (5.0%, 15 mL) was added to the orange solid with stirring at 0-7° C. After 17 hours the mixture formed a thick viscous brown liquid with a high amount of undissolved suspended solid. The resultant mixture was deemed to be unsuitable for the efficient production of viscose fibres and articles of manufacture.

Example 10

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and dried in an oven at 105° C. Sodium hydroxide pellets (27.08 g) was added to deionised water (150 mL) and vigorously stirred in a cold water bath until the pellets were dissolved. The sodium hydroxide solution was added to the prepared dried microbial cellulose solid (3.010 g) and blended in a 375 W Waring Variable Speed Laboratory blender at the maximum speed setting for 3 minutes to afford a 2.0% reaction mixture pulp. The reaction mixture was stirred at 50° C. for 98 minutes before the hot reaction mixture was vacuum filtered through a Buchner funnel to yield a pale brown moist hard solid. The solid was then pressed between dry Whatman filter paper (grade 1) two times before being transferred to a tared 100 mL two necked round bottom flask. The net weight of the solid was 9.093 g (press factor=3.02). The reaction vessel was evacuated via a pump and sealed from the outside atmosphere with a septum and allowed to rest overnight at room temperature for 16 hours. Carbon disulfide (1.09 g, 0.86 mL, 0.0143 mol) was then introduced to the reaction flask through a septum via syringe which was then gently agitated before being allowed to stand in a water bath at 32° C. After 60 minutes the solid became bright orange in colour where upon the septum was removed and the mixture was exposed to air for 1 minute. The flask was resealed with the septum and then immersed in an ice bath for 5 minutes before sodium hydroxide solution (5.0%, 30 mL) was added to the orange solid with stirring at 0-7° C. After 6 hours the mixture remained unchanged, a wet orange solid. The mixture was then allowed to stir at room temperature for 17 hours and remained unchanged. No dissolution had occurred.

Example 11

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp that was then passed through a 1 mm$^2$ pore size deckle to form a wet solid sheet. The sheet was then freeze dried for one day to afford a dry white sheet.

The sheet was then cut into smaller squares (10 mm$^2$, 20 g) and then added to 18% sodium hydroxide solution (800 mL) and mechanically stirred for 30 minutes at 50° C. The reaction mixture was then pressed at constant pressure at 70 kp cm$^{-2}$ to obtain a target press factor of 2.8. A press factor of 3.45 could be achieved. The resulting alkali cellulose was then shredded using a tempered shredder for 45 minutes where the mill was run in three periods of 13 minutes forward and 2 minutes backwards. The shredded solid was isolated in a glass bottle with air and covered with perforated para film being agitated periodically every 30 minutes at 50° C. After 6 hours the aged solid was then transferred to a closed reaction vessel. Carbon disulfide (7.2 g, 5.7 mL. 0.0946 mol) was then introduced to the reaction vessel through a septum via syringe under vacuum. The reaction mixture was agitated by rotating the reaction vessel in a water bath at 32° C. The vacuum in the reaction vessel was maintained. After 150 minutes the solid became an orange solid. 10% Sodium hydroxide solution (105 mL) was added to the orange solid at 7° C. with stirring for 10 minutes and then deionised water (105 mL) was added to the mixture. The mixture was then agitated via rotation for 180 minutes hours at 7° C. Most of the solid dissolved to afford a brown viscous liquid consisting of some suspended white particulate matter. The mixture was then allowed to stand at room temperature for 16 hours to give a viscous liquid that was brown consisting of white particulate matter (cellulose content=9.13%, 250 mL g$^{-1}$, undissolved akali cellulose/xanthate=4.0%, ripening index=9). Due to the high undissolved akali cellulose/xanthate content of 4.0%, this liquid could not be spun for the production of fibres. This was attempted to be overcome with a two-step filtration by filtering through a 100 μm filter followed by a 30 μm filter which also proved not to be efficient, providing only the production of 1.6 g (fibre yield=8.0%) of fibres before the spinning instrument was blocked and thus deemed unsuitable for the wide production of viscose dope. This small amount of viscose dope recovered was able to be spun into a fibre, using standard viscose conditions, having the following values; tenacity 14.22 cN/tex, elongation 15.75% & titer 2.77 dtex.

Example 12

Microbial cellulose sheets were produced by growing cellulose producing bacteria in a liquid culture medium containing a carbon source, nutrients, water and other growth factors. This cellulose producing bacterium is *Acetobacter xylinum*, a rod shaped Gram-negative bacteria that are 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This media contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach an approximate 10 mm thickness, at optimum growth conditions, in 8-12 days. Harvesting involves removing the microbial cellulose sheets from the culture vessels and washing in water. The sheets are dried in the sun or by using external heat such as drying rooms to a moisture content less than 5%.

Microbial cellulose sheet (5.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The treated squares (5.0 g) were then isolated via a sieve and added to fresh water (1.0 L) and then boiled for 20 minutes. The mixture was cooled to room temperature and the squares were isolated and dried in an oven at 105° C. for 6 hours. The dried solid (3.0 g) was added to deionised water (400 mL) and blended for 3 minutes using the 600 W Nutribullet with extractor blade to afford a homogenous thick white pulp (7.5 g L$^{-1}$, particle size: D10=47 μm, D50=268 μm, D90=943 μm, M$_w$=1,005,257, PD=3.8).

Sodium hydroxide pellets (36.1 g, 0.903 mol) were added to deionised water (66 mL) and stirred in a cold water bath until the pellets dissolved. The microbial cellulose pulp (133 mL) was then added to the sodium hydroxide solution and the resulting mixture was vigorously stirred briefly for 5 minutes at room temperature causing the resultant pulp to uniformly disperse. The reaction mixture was then heated and gently stirred at 50° C. for 2 hours before the hot reaction mixture was quickly vacuum filtered through a Buchner funnel to yield a wet off-white solid. The solid was then pressed between Whatman filter paper (grade 1) several times until no further liquid could be expressed before being transferred to a tared 100 mL two necked round bottom flask fitted with a rubber septum and gas adaptor with tap. The net weight of the solid was 3.99 g (press factor=4.0). The reaction vessel was evacuated via a vacuum pump and sealed from the outside atmosphere with the septum. Carbon disulfide (0.35 g, 0.28 mL, 4.60 mmol) was then introduced to the reaction flask through a septum via syringe which was then gently agitated before being allowed to stand in a water bath at 30-34° C. After 60 minutes the solid became bright orange and sticky where upon the septum was removed and the mixture was exposed to air for 1 minute. The flask was resealed with the septum and then immersed in an ice bath for 5 minutes. Sodium hydroxide solution (5.0%, 11 mL) was added to the orange solid with stirring at 0-5° C. The mixture was stirred in the ice-bath (10-19° C.). After 16 hours the orange mixture became a clear brown viscous liquid; viscose dope (cellulose content=9.1% wt/vol).

The resulting viscose dope was loaded onto a 10 mL syringe with a luer lock needle (0.8 mm gauge) and the tip was submerged in a regeneration solution of 130 g $L^{-1}$ sulfuric acid, 310 g $L^{-1}$ sodium sulfate, 9.5 g $L^{-1}$ zinc sulfate. The viscose dope was extruded via the syringe into the regeneration bath to produce white fibres that were allowed to sit in the regeneration bath for a few minutes before being thoroughly washed in water and then allowed to dry in air stretched on a glass pane. Example 13 (viscose dope from never-dried microbial cellulose pellicles)

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose pellicles reach approximately 10 mm thickness, at optimum growth conditions, in 8-12 days. Harvesting involves removing the microbial cellulose sheets from the culture vessels and washing with water. The microbial cellulose pellicles (109.85 g, approx. 0.84 g cellulose) were then stick blended for ~2 minutes using the 300 W Braun Multiquick 1 Hand Processor to afford a pale pink sludge (approx. cellulose concentration=7.6 g $L^{-1}$).

Sodium hydroxide pellets (36.99 g, 0.925 mol) were added to deionised water (59.07 g) and stirred until the pellets dissolved. The microbial cellulose sludge was then added to the warm sodium hydroxide solution and the resulting mixture (cellulose concentration=5.0 g $L^{-1}$) was stirred at 50° C. for 120 minutes. The reaction mixture was a deep brown/red colour which was then vacuum filtered through a Buchner funnel to yield a wet pale pink solid. The solid was then pressed between Whatman filter paper (grade 1) several times until no further liquid could be expressed before being transferred to a tared 100 mL two necked round bottom flask fitted with a rubber septum and gas adaptor with tap. The net weight of the solid was 3.08 g (press factor=3.7). The reaction vessel was evacuated via a vacuum pump and sealed from the outside atmosphere with the septum. Carbon disulfide (0.30 g, 0.24 mL, 4.0 mmol) was then introduced to the reaction flask through a septum via syringe which was then gently agitated before being allowed to stand in a water bath at 30-34° C. After 60 minutes the solid became a dull orange where upon the septum was removed and the solid was exposed to the air for 1 minute. The flask was resealed with the septum and then immersed in an ice bath for 5 minutes. Sodium hydroxide solution (5.0%, 8.84 mL) was added to the orange solid with stirring at 0-5° C. After 3 hours the mixture changed from a sticky mass with suspended solids to a very viscous orange liquid; viscose dope (cellulose content=6.6 wt/wt %).

Example 14

This example demonstrates that detergent use is optional.

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose pellicles reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Dried microbial cellulose sheet (5.0 g) was cut into 24 mm² squares and added to water (1.0 L) to form a suspension. The suspension was boiled for ~30 minutes and then the squares were isolated via a sieve and added to deionised water (1.11 L) and blended for 3 minutes using the 600 W Nutribullet with extractor blade to afford a homogenous fine white pulp (4.5 g $L^{-1}$). Sodium hydroxide pellets (54.0 g, 1.35 mol) were added to deionised water (70 mL) and stirred in a cold water bath until pellets dissolved. The microbial cellulose pulp (230 mL) was then added to the sodium hydroxide solution and the resulting mixture (cellulose concentration=3.3 g $L^{-1}$) was then gently stirred at 50° C. for 110 minutes before the hot reaction mixture was quickly vacuum filtered through a Buchner funnel to yield a wet off white solid. The solid was then pressed between Whatman filter paper (grade 1) several times until no further liquid could be expressed before being transferred to a tared 100 mL two necked round bottom flask fitted with a rubber septum and gas adaptor with tap. The net weight of the solid was 5.8 g (press factor=5.6). The reaction vessel was evacuated via a vacuum pump, and carbon disulfide (0.36 g, 0.28 mL, 0.0047 mol) was then introduced to the reaction flask through the septum via syringe. The reaction flask was then gently agitated before being allowed to stand in a water bath at 30-34° C. After 75 minutes the solid became a light orange and sticky where upon the septum was removed and the solid was exposed to air for 1 minute. The flask was resealed with the septum and then immersed in an ice bath for 5 minutes. Sodium hydroxide solution (5.0%, 12 mL) was added to the orange solid with stirring at 0-5° C. After 17 hours the mixture was a homogeneous orange viscous liquid; viscose dope (cellulose content=8%).

Example 15

This example demonstrates mercerisation using solid sodium hydroxide.

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 µm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose pellicles reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%. The sheets are mechanically shredded into flakes of approximately 24 mm$^2$. Microbial cellulose flakes (2.05 g) were added to water (400 mL) to form a suspension. The suspension was heated to 100° C. for 2 minutes and then Biozet Attack laundry detergent (Kao Corporation) (0.5 g) was added to the mixture which was then boiled for 25 minutes. The treated flakes (2.05 g) were then isolated via a sieve and added to fresh water (400 mL) and then boiled for 20 minutes. The mixture was cooled to room temperature and the squares were isolated via sieve allowed to oven dry at ~50° C. for one day. The dry flakes were added to deionised water (198 mL) and then blended for 3 minutes using the 600 W Nutribullet with extractor blade to afford a homogeneous thick white pulp (10.3 g L$^{-1}$).

Sodium hydroxide pellets (43.75 g, 1.094 mol) were then added to the white pulp and stirred until pellets dissolved. The resulting mixture (cellulose concentration=9.9 g L$^{-1}$) was then gently stirred at 50° C. for 2 hours before the warm reaction mixture was quickly vacuum filtered through a Buchner funnel to yield a wet white filter cake. The cake was then pressed between Whatman filter paper (grade 1) several times until no further liquid could be expressed before being transferred to a tared 100 mL two necked round bottom flask fitted with a rubber septum and gas adaptor with tap. The net weight of the solid was 7.71 g (press factor=3.8). The reaction vessel was then allowed to stand in a water bath at 50° C. for 71 minutes. Some condensation had formed and was removed with paper towel. The reaction vessel was then allowed to cool to room temperature before the air was evacuated via a vacuum pump. Carbon disulfide (0.72 g, 0.57 mL, 9.5 mmol) was then introduced to the reaction flask through a septum via syringe which was then gently agitated before being allowed to stand in a water bath at 30-34° C. After 51 minutes the solid became an orange and sticky solid whereupon the septum was removed and the mixture was exposed to air for 1 minute. The flask was resealed with the septum and then immersed in an ice bath for 5 minutes. Sodium hydroxide solution (5.01 wt/wt %, 21.05 mL) was added to the orange solid with stirring at 0-5° C. After 16 hours the mixture changed from a sticky mass to a viscous homogeneous orange liquid; viscose dope (cellulose content=9.5%, ball fall20 cm=59 seconds), clearly suitable for production of a viscose fibre.

Example 16

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 µm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Dry microbial cellulose sheet (20.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp.

The pulp was added to a sodium hydroxide solution to make a final 18% sodium hydroxide mercerization solution and mechanically stirred for 120 minutes at 50° C. The reaction mixture was then pressed at constant pressure at 70 kp cm$^{-2}$ to obtain a target press factor. A press factor of 4.5 could be achieved. The resulting alkali cellulose was then isolated in a glass bottle with air and covered with perforated para film being agitated at 50° C. for 235 mins. After a targeted intrinsic viscosity of 250 g/ml was achieved, the aged solid was then transferred to a closed reaction vessel. Carbon disulfide (final dosage ~48.5%) was then introduced to the reaction vessel through a septum via syringe under vacuum. The reaction mixture was agitated by rotating the reaction vessel in a water bath at 32° C. The vacuum in the reaction vessel was maintained. After 50 minutes the solid became an orange solid. 5% sodium hydroxide solution was added to the orange solid with stirring for 180 minutes at 7° C. All of the solid dissolved to afford a brown viscous liquid. The mixture was then allowed to stand at room temperature for 16 hours to give a viscous liquid that was brown consisting of (cellulose content=5.8%, Kr value of 307, ball fall of 6 s and a gamma number 40). This viscose dope was able to be spun into a fibre, using standard viscose conditions, having the following values; tenacity 16.24 cN/tex, elongation 15.47% & titer 1.49 dtex.

Example 17

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Microbial cellulose sheet (20.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water (0.5-1 L) using the 600 W Nutribullet with extractor blade affording a thick white pulp.

The pulp was added to a sodium hydroxide solution to make a final 18% sodium hydroxide mercerization solution and mechanically stirred for 120 minutes at 50° C. The reaction mixture was then pressed at constant pressure at 70 kp cm$^2$ to obtain a target press factor. A press factor of 4.5 could be achieved. The resulting alkali cellulose was then isolated in a glass bottle with air and covered with perforated para film being agitated at 50° C. for 235 mins. After a targeted intrinsic viscosity of 250 g/ml was achieved, the aged solid was then transferred to a closed reaction vessel. Carbon disulfide (final dosage 36%) was then introduced to the reaction vessel through a septum via syringe under vacuum. The reaction mixture was agitated by rotating the reaction vessel in a water bath at 32° C. The vacuum in the reaction vessel was maintained. After 50 minutes the solid became an orange solid. 5% sodium hydroxide solution was added to the orange solid with stirring for 180 minutes at 7° C. All of the solid dissolved to afford a brown viscous liquid. The mixture was then allowed to stand at room temperature for 16 hours to give a viscous liquid that was brown consisting of (cellulose content=8.6%, Kr value of 472, ball fall of 29 s and a gamma number 35). This viscose dope was able to be spun into a fibre, using standard viscose conditions, having the following values; tenacity 19.00+cN/tex, elongation 14.25% & titer 2.09 dtex.

Example 18

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water.

For the purposes of this experiment, the sample was split and only a portion was dried to deliver a moisture content of less than 5%.

Samples of both the never-dried or dry microbial cellulose sheets were macerated with water using a NutriBullet Rx food processor (shear force) into a 1% microbial cellulose content pulp. The times were varied to determine the effect the step of homogenising the microbial cellulose pulp had on the particle size and the fibrous masses of microbial cellulose.

A particle size distribution analysis of each sample was undertaken using the Mastersizer 2000 laser diffractometer as described above. The results are shown in Table 1 below:

TABLE 1

| Particle Size Distribution Analysis | | | | |
|---|---|---|---|---|
| MC Source | Blend Time (sec) | d (0.1) | d (0.5) | d (0.9) |
| Never-Dried | 30 | 26.091 | 204.102 | 890.813 |
|  | 60 | 5.241 | 91.238 | 433.464 |
|  | 90 | 1.433 | 71.442 | 320.195 |
|  | 120 | 1.202 | 65.35 | 243.095 |

TABLE 1-continued

| | Particle Size Distribution Analysis | | | |
|---|---|---|---|---|
| MC Source | Blend Time (sec) | d (0.1) | d (0.5) | d (0.9) |
| | 180 | 1.278 | 59.056 | 228.464 |
| | 300 | 1.169 | 47.625 | 168.017 |
| Washed-Dried | 30 | 453.39 | 1010.865 | 1595.021 |
| | 60 | 117.658 | 617.944 | 1389.803 |
| | 90 | 93.159 | 548.745 | 1333.38 |
| | 120 | 45.983 | 244.685 | 942.001 |
| | 180 | 31.674 | 157.718 | 611.641 |
| | 300 | 25.177 | 125.545 | 464.778 |

As expected, the step of homogenising the microbial cellulose pulp reduced the measured particles size distribution of the microbial cellulose particles. The longer the homogenisation step was conducted, the smaller the particle size distribution. Using polarising lenses and 20× magnification, images were taken of each sample to qualitatively compare the effect the blend time had on the microbial cellulose in the pulp. The 30 second blend time pulps exhibited many microbial cellulose flakes that were not fibrillated. As the blend time was increased to 60 seconds the number of microbial cellulose flakes decreased. When the blend time was increased to 90 seconds, even fewer microbial cellulose flakes remained. For the 120 second pulp, it was observed that most of the microbial cellulose flakes had fibrillated well. The extent of fibrillation further increased for the 180 second and 300 second pulps.

Comparison of the the data received from the Mastersizer 2000 and the observations made showed a strong correlation between the reduction of the particle size and the extent of fibrillation.

Example 19

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Deionised water (198 g) was added to washed and chipped dried microbial cellulose flakes (2.0 g) and then blended in the 600 W Nutribullet with extractor blade. Separate samples were taken at 10 minutes, 20 minutes and 30 minutes total blending time. The blending was paused every ~2-3 minutes to allow the blender to cool before resuming blending.

A particle size distribution analysis of each sample was undertaken using the Mastersizer 2000 laser diffractometer as described above. The results are shown in Table 2 below:

TABLE 2

| | Particle Size Distribution Analysis | | | |
|---|---|---|---|---|
| MC Source | Blend Time (sec) | d (0.1) | d (0.5) | d (0.9) |
| Washed-Dried | 600 | 22.067 | 127.757 | 596.558 |
| — | 1200 | 15.871 | 102.643 | 409.995 |
| — | 1800 | 8.243 | 52.477 | 153.296 |

As expected, the step of homogenising the microbial cellulose pulp reduced the measured particles size distribution of the microbial cellulose particles. The longer the homogenisation step was conducted, the smaller the particle size distribution.

Example 20

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

6 samples of 1.0 wt/wt % microbial cellulose pulp were prepared from 2 g of dried microbial cellulose. Each samples was subjected to a homogenisation step with a different blend time. The particle size of the microbial cellulose pulp was measured in using the Mastersizer 2000 laser diffractometer as described above.

Each separate pulp was added to a sodium hydroxide solution to make a final 18% sodium hydroxide mercerization solution and mechanically and magnetically stirred for 120 minutes at 50° C. The reaction mixture was then pressed between grade 1 Whatman filter paper by hand four times, each time with a new filter paper to obtain a press factor. The resulting alkali cellulose was then isolated in a closed two necked round bottom flask fitted with a septum and gas adaptor. The air was then evacuated from the reaction vessel via a vacuum pump and then carbon disulfide (36% of cellulose mass) was then introduced through the septum via syringe. The reaction mixture was then briefly agitated and then the reaction vessel was left to stand in a water bath at 32° C. After 70-80 minutes the solid became an orange solid that was slightly sticky. The vacuum of the reaction vessel was released and the solid was exposed to normal air briefly before being sealed and then cooled in an ice bath for 5 minutes. 5.0% sodium hydroxide solution was added to the orange solid with magnetic stirring whilst in the ice bath. The solid was left to stir overnight in the ice bath maintain a temperature between 0-7° C. for 3 hours and then slowly increasing to 21° C. After ~16 hours the solid dissolved to afford a viscous orange liquid (except in the case when a 30 second blended pulp was used which gave a clumpy non homogeneous orange mixture).

Once the viscose dopes were produced, the gel content of the viscous liquid was measured. Each of the viscose dopes obtained were diluted (20x) with D.I water and then stirred for ~20 minutes to give a homogenous orange liquid which was then vacuum filtered through a Buchner funnel fitted with a pre-weighed 20 micron or 8 micron Whatman filter paper. The filter paper was then dried in an oven at 40° C. until completely dry and then weighed. The mass difference of the filter paper before and after filtration and dried was assumed to be the "gel content". The % gel content was then calculated by mass of the viscose dope diluted. The results are shown in Table 3.

As expected, the particle size of the microbial cellulose pulp decreased with increased blend times, as did the press factor. This suggests that the larger particles hold on to moisture more readily, and the press factor can be controlled by altering the blend time of the pulp.

The results showed that the gel content generally decreased with longer blend times. The 90 second blend time appears to be an outlier. This suggests that the reduction in the particle size in the pulp will cause the pulp to be more amenable to the mercerisation/xanthation process. Without wishing to be bound by theory, the inventors believe that the reduction is particle size will act to fibrillate the dense microbial cellulose network, thereby allowing greater contact with the NaOH.

Example 21

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 μm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The starting material was washed with copious amounts of water to remove residual acetic acid and was never dried.

A series of tests were undertaken to determine the effect of blend time of the raw microbial cellulose pellicle had on the gel content of the resultant viscose dope. The cellulose content of each pellicle was measured by drying and recording the mass difference to obtain the true mass of cellulose in the reaction. Though the cellulose content of the microbial cellulose pellicles varied substantially, the average for a thick pellicle was 1-2%. Pellicles were selected to obtain a

TABLE 3

MC Pulping times v Particle Size and resultant viscose dope gel content (n = 1)

| Blend Time (seconds) | d (0.1) | d (0.5) | d (0.9) | Press Factor | Gel Content (>20 μm) (wt. %) | Gel Content (>8 μm) (wt. %) |
|---|---|---|---|---|---|---|
| 30 | 453.390 | 1010.865 | 1595.021 | 5.4 | 1.82 | 1.95 |
| 60 | 117.658 | 617.944 | 1389.803 | 4.6 | 0.69 | 0.67 |
| 90 | 93.159 | 548.745 | 1333.380 | 4.3 | 0.15 | 0.87 |
| 120 | 45.983 | 244.685 | 942.001 | 4.5 | 0.31 | 0.71 |
| 180 | 31.674 | 157.718 | 611.641 | 4.1 | 0.33 | 0.64 |
| 300 | 25.177 | 125.545 | 464.778 | 4.0 | 0.06 | 0.43 |

1.0 wt/wt % pulp containing 2.0 g of cellulose. Six samples of pulp were prepared at different blend times as tabulated below. The particle size distribution of the pulp was measured using the Mastersizer 2000.

Each separate pulp was added to a sodium hydroxide solution to make a final 18% sodium hydroxide mercerization solution and mechanically and magnetically stirred for 120 minutes at 50° C. The reaction mixture was then pressed between grade 1 Whatman filter paper by hand four times, each time with a new filter paper to obtain a press factor. The resulting alkali cellulose was then isolated in a closed two necked round bottom flask fitted with a septum and gas adaptor. The air was then evacuated from the reaction vessel via a vacuum pump and then carbon disulfide (36% of cellulose mass) was then introduced through the septum via syringe. The reaction mixture was then briefly agitated and then the reaction vessel was left to stand in a water bath at 32° C. After 70-80 minutes the solid became an orange solid that was slightly sticky. The vacuum of the reaction vessel was released and the solid was exposed to normal air briefly before being sealed and then cooled in an ice bath for 5 minutes. 5.0% sodium hydroxide solution was added to the orange solid with magnetic stirring whilst in the ice bath. The solid was left to stir overnight in the ice bath maintain a temperature between 0-7° C. for 3 hours and then slowly increasing to 21° C. After ~16 hours the solid dissolved to afford a viscous orange liquid (except in the case when a 30 second blended pulp was used which gave a clumpy non homogeneous orange mixture).

Once the viscose dopes were produced, the gel content of the viscous liquid was measured. Each of the viscose dopes obtained were diluted (20×) with D.I water and then stirred for ~20 minutes to give a homogenous orange liquid which was then vacuum filtered through a Buchner funnel fitted with a pre-weighed 8 micron Whatman filter paper. The filter paper was then dried in an oven at 40° C. until completely dry and then weighed. The mass difference of the filter paper before and after filtration and dried was assumed to be the "gel content". The % gel content was then calculated by mass of the viscose dope diluted. The results are shown in Table 4.

to be more amenable to the mercerisation/xanthation process. Without wishing to be bound by theory, the inventors believe that the reduction is particle size will act to fibrillate the dense microbial cellulose network, thereby allowing greater contact with the NaOH. Furthermore, when compared with the results of Example 19, the viscose dope prepared from never-dried microbial cellulose proved to have lower gel content than the viscose dope that was prepared from washed & dried microbial cellulose. Without wishing to be bound by theory, the inventors believe that his is most probably due to the fact that the never-dried microbial cellulose is much more accessible to react with NaOH given the abundance of water in the pellicle which serves to disrupt the hydrogen bonding network between the cellulose polymers (intermolecular and inter-sheet bonding).

Example 22

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 µm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days.

TABLE 4

Never-dried MC pulping time's v particle size and resultant viscose dope gel content

| Sample | Blend Time (seconds) | Particle Size of Pulp (µm) | | | Press Factor | Gel Content (>8 µm) (wt/wt %) |
|---|---|---|---|---|---|---|
| | | d (0.1) | d (0.5) | d (0.9) | | |
| 1 | 30 | 26.091 | 204.102 | 890.813 | ~2.9 | 0.27 |
| 2 | 60 | 5.241 | 91.228 | 433.464 | ~2.4 | 0.62 |
| 3 | 90 | 1.433 | 71.442 | 320.195 | ~1.6 | 0.11 |
| 4 | 120 | 1.202 | 65.350 | 243.095 | n/a | 0.76 |
| 5 | 180 | 1.278 | 59.056 | 228.464 | ~2.0 | 0.44 |
| 6 | 300 | 1.169 | 47.625 | 168.017 | ~2.1 | 0.036 |

As expected, the particle size of the microbial cellulose pulp decreased with increased blend times, as did the press factor. This suggests that the larger particles hold on to moisture more readily, and the press factor can be controlled by altering the blend time of the pulp.

The results showed that the gel content generally decreased with longer blend times. The 30 and 90 second blend times appear to be an outliers. This suggests that the reduction in the particle size in the pulp will cause the pulp Harvesting involves removing the microbial cellulose sheets from the culture vessels and washing with water. The sheets can be sun dried or by drying rooms to deliver a moisture content of less than 5%.

Dry microbial cellulose sheet (20.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water at 1% using the 600 W Nutribullet with extractor blade for 120 s affording a thick white pulp. Separate samples of the pulp were concentrated at 1.5%, 2%, 3%, 4% and 5%.

Each separate pulp was added to a sodium hydroxide solution to make a final 18% sodium hydroxide mercerization solution and mechanically stirred for 120 minutes at 50° C. The reaction mixture was then pressed at constant pressure at 70 kp cm$^{-2}$ to obtain a press factor. The resulting alkali cellulose was then isolated in a glass bottle with air and covered with perforated para film being agitated at 50° C. for 235 mins. After a targeted intrinsic viscosity of 250 g/ml was achieved, the aged solid was then transferred to a closed reaction vessel. Carbon disulfide (final dosage 36%) was then introduced to the reaction vessel through a septum via syringe under vacuum. The reaction mixture was agitated by rotating the reaction vessel in a water bath at 32° C. The vacuum in the reaction vessel was maintained. After 50 minutes the solid became an orange solid. 5% sodium hydroxide solution was added to the orange solid with stirring for 180 minutes at 7° C. All of the solid dissolved to afford a brown viscous liquid. The mixture was then allowed to stand at room temperature for 16 hours to give a viscous liquid.

The the gel content measured by diluting the dope with water (20×) and filtering through filter paper (pore size 8 µm), washed thoroughly with water and air dried for 48 hours. The results are shown is Table 5 below.

TABLE 5

Gel Content Measurements

| Pulp concentration (%) | Gel content (wt/wt %) |
|---|---|
| 1 | 0 |
| 1.5 | 0.059 |
| 2 | 0.133 |
| 3 | 0.217 |
| 4 | N/A |
| 5 | N/A |

The results showed that the increase in microbial cellulose concentration in the pulp led to an increase in gel content in the dope. As the pulp concentration increased from 2% through to 4% the number of fibrous masses that remained in the dope gradually increased. At 4%, the dope had many visible and large undissolved particles. It is envisaged by the inventors that in order for these dopes to be used commercially, significant filtration will be required. It was observed that as the concentration of the pulp exceeded 4%, the pulp began to exhibit handling problems that are highly undesirable for further processing. The pulp did not behave as a fluid pulp and this prevented adequate reaction of the cellulose with the sodium hydroxide during mercerisation. This resulted in a significant increase in the number of fibrous masses of microbial cellulose remaining in the mercerised pulp. Whilst it may be possible to selectively remove these aggregates through filtrations, the amount of filtration required is unlikely to be commercially practical.

Example 23

Microbial cellulose sheets were produced by growing a cellulose producing bacteria in a liquid culture medium containing a carbon source, nutrients, water and other growth factors. This cellulose producing bacterium is *Acetobacter xylinum*, a rod shaped Gram-negative bacteria that is 1-4 µm in size. Under aerobic conditions, *A. xylinum* converts carbon sources such as, but not limited to, glucose, sucrose and ethanol into large quantities of pure cellulose micro fibrils.

The most common culture medium that is used to grow *A. xylinum* is a modified Hestrin and Schramm, 1954. This medium contains; 2% (w/v) glucose, 0.5% (w/v) peptone (Difco bactopeptone), 0.5% (w/v) yeast extract (Difco), 0.27% anhydrous disodium phosphate, 0.15% (w/v) citric acid monohydrate, kept at pH 5 using acetic acid, optimum temperature 30° C.

One alternative medium is to add coconut milk or coconut water to the liquid at a final concentration of 20-50% respectively as a substitute for the nutrients. Another is to add wine and beer at a final ethanol concentration of 5-8% as a substitute for the nutrients.

The microbial cellulose sheets reach approximately 10 mm thickness, at optimum growth conditions, in 8-12 days. Harvesting involves removing the microbial cellulose sheets from the culture vessels and washing with water. The sheets can be sun dried or by drying rooms to deliver a moisture content of less than 5%.

Dry microbial cellulose sheet (20.0 g) was cut into 24 mm$^2$ squares and added to water (1.0 L) to form a suspension. The suspension was heated to 100° C. for 2 minutes and then Biozet Attack laundry detergent (Kao Corporation) (1.25 g) was added to the mixture which was then boiled for 25 minutes. The squares (5.0 g) were then isolated via a sieve and added to fresh water (1.0 L) and then boiled for 20 minutes. The mixture was cooled to room temperature and the squares were isolated via a sieve and then blended in water at 1% using the 600 W Nutribullet with extractor blade for 120 s affording a thick white pulp. Separate samples of the pulp were concentrated at 1.5%.

Each separate pulp was added to a sodium hydroxide solution to make a final 18% sodium hydroxide mercerization solution and mechanically stirred for 120 minutes at 50° C. The reaction mixture was then pressed at constant pressure at 70 kp cm$^{-2}$ to obtain a press factor. The resulting alkali cellulose was then isolated in a glass bottle with air and covered with perforated para film being agitated at 50° C. for 235 mins. After a targeted intrinsic viscosity of 250 g/ml was achieved, the aged solid was then transferred to a closed reaction vessel. Carbon disulfide (final dosage 36%) was then introduced to the reaction vessel through a septum via syringe under vacuum. The reaction mixture was agitated by rotating the reaction vessel in a water bath at 32° C. The vacuum in the reaction vessel was maintained. After 50 minutes the solid became an orange solid.

5% sodium hydroxide solution was added to the orange solid with stirring at 7° C. for set period of time. In order to understand the impact that the stirring time had on the gel content of the viscose dope, samples of each the 1.0 wt/wt % and 1.5 wt/wt % were stirred for 0.5, 3.0 and 18 hours respectively.

Following the completion of the stirring, each mixture was then allowed to stand at room temperature for 16 hours to give a viscous liquid.

The gel content of each sample was measured by diluting the dope with water (20×) and filtering through filter paper (pore size 8 µm), washed thoroughly with water and air dried for 48 hours. The results are shown is Table 6 below.

TABLE 6

Gel Content Measurements

| MC Concentration | Stirring Time | Gel Content | Observations |
|---|---|---|---|
| 1.5 wt/wt % | 0.5 hours | 1.50% | Viscose dope that was thick with a lot of undissolved solid. Separated into two layers. The bottom layer was very thick, dense and viscous. The top layer was thin, fluid and slightly viscous. |
| 1.5 wt/wt % | 3 hours | 0.53% | Viscose dope, with some undissolved solid |
| 1.5 wt/wt % | 18 hours | 0.29% | Viscose dope with few undissolved solid |
| 1.0 wt/wt % | 0.5 hours | 0.46% | Viscose dope with very few, very small undissolved solids. Dope was separated into two layers like first entry |
| 1.0 wt/wt % | 3 hours | 0.17% | Good viscose dope |
| 1.0 wt/wt % | 18 hours | 0.11% | Good viscose dope |

The results showed that the increase in the stirring time during the step of dissolution led to a reduction in the gel content of the final viscose dope. As would be appreciated by a person skilled in the art, it is well understood that when dissolving cellulose xanthates produced from cellulose pulps derived from wood, any particles that have not dissolved after approximately 2 to 3 hours of contact with an aqueous solution of sodium hydroxide are unlikely to dissolve. The results shown that by conducting the step of contacting the microbial cellulose xanthate with an aqueous solution of sodium hydroxide with agitation for a period longer than that typically used for dissolving xanthates produced from cellulose-pulps derived from wood, the greater the extent of dissolution of particles.

The invention claimed is:

1. A method for producing a viscose dope, the method comprising steps of:
    exposing a microbial cellulose to a volume of water to form a microbial cellulose pulp, wherein the cellulose concentration in the microbial cellulose pulp is less than 0.040 g of cellulose per mL of pulp;
    homogenising the microbial cellulose pulp;
    exposing the microbial cellulose pulp to a quantity of sodium hydroxide solution to produce a mercerised microbial cellulose pulp, wherein the cellulose concentration in the mixture of microbial cellulose pulp and sodium hydroxide solution is less than 0.035 g of cellulose per mL of mixture;
    treating the mercerised microbial cellulose pulp with carbon disulphide to produce a microbial cellulose xanthate; and
    contacting the microbial cellulose xanthate with an aqueous solution of sodium hydroxide to produce a microbial cellulose viscose dope.

2. The method according to claim 1, wherein the homogenising of the microbial cellulose pulp produces a particle size distribution of particles of cellulose having a D90 of less than 1700 µm.

3. The method according to claim 1, wherein the homogenising of the microbial cellulose pulp produces a particle size distribution of particles of cellulose having a D50 of less than 1200 µm.

4. The method according to claim 1, wherein the homogenising of the microbial cellulose pulp produces a particle size distribution of particles of cellulose having a D10 of less than 500 µm.

5. A method for the production of viscose rayon fibres, the method comprising:
    exposing a microbial cellulose to a volume of water to form a microbial cellulose pulp, wherein the cellulose concentration in the microbial cellulose pulp is less than 0.040 g of cellulose per mL of pulp;
    homogenising the microbial cellulose pulp such that the particle size distribution of the particles of cellulose in the pulp has a D90 of less than 1700 µm, a D50 of less than 1200 µm and a D10 of less than 500 µm;
    exposing the microbial cellulose pulp to a quantity of sodium hydroxide solution to produce a mercerised microbial cellulose pulp, wherein the cellulose concentration in the mixture of microbial cellulose pulp and sodium hydroxide solution is less than 0.035 g of cellulose per mL of mixture;
    treating the mercerised microbial cellulose pulp with carbon disulphide to produce a microbial cellulose xanthate; and
    contacting the microbial cellulose xanthate with an aqueous solution of sodium hydroxide to produce a microbial cellulose viscose dope; and
    regenerating viscose rayon fibres from the microbial cellulose viscose dope.

6. The method according to claim 5, wherein the regenerating step comprises extruding the microbial cellulose into a regeneration solution to produce viscose rayon fibres.

7. A method for the production of a viscose sheet, the method comprising:
    exposing a microbial cellulose to a volume of water to form a microbial cellulose pulp, wherein the cellulose concentration in the microbial cellulose pulp is less than 0.040 g of cellulose per mL of pulp;
    homogenising the microbial cellulose pulp such that the particle size distribution of the particles of cellulose in the pulp has a D90 of less than 1700 µm, a D50 of less than 1200 µm and a D10 of less than 500 µm;
    exposing the microbial cellulose pulp to a quantity of sodium hydroxide solution to produce a mercerised microbial cellulose pulp, wherein the cellulose concentration in the mixture of microbial cellulose pulp and sodium hydroxide solution is less than 0.035 g of cellulose per mL of mixture;
    treating the mercerised microbial cellulose pulp with carbon disulphide to produce a microbial cellulose xanthate; and
    contacting the microbial cellulose xanthate with an aqueous solution of sodium hydroxide to produce a microbial cellulose viscose dope; and
    regenerating a sheet of viscose from the microbial cellulose viscose dope.

8. The method according to claim 7, wherein the regenerating step comprises extruding a film of the microbial cellulose viscose dope into a regeneration solution to produce a sheet of viscose.

* * * * *